United States Patent
Austin et al.

(10) Patent No.: US 8,940,028 B2
(45) Date of Patent: Jan. 27, 2015

(54) SYSTEMS AND METHODS FOR USING POLYAXIAL PLATES

(75) Inventors: Gene Edward Austin, Bartlett, TN (US); Jon Andrew Harmon, Byhalia, MS (US); Sied W. Janna, Memphis, TN (US); James K. Rains, Cordova, TN (US); John B. Schneider, Memphis, TN (US); Timothy J. Petteys, Millington, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1812 days.

(21) Appl. No.: 11/996,795

(22) PCT Filed: Jul. 25, 2006

(86) PCT No.: PCT/US2006/028778
§ 371 (c)(1),
(2), (4) Date: Aug. 1, 2008

(87) PCT Pub. No.: WO2007/014192
PCT Pub. Date: Feb. 1, 2007

(65) Prior Publication Data
US 2009/0143824 A1    Jun. 4, 2009

Related U.S. Application Data

(60) Provisional application No. 60/702,231, filed on Jul. 25, 2005.

(51) Int. Cl.
*A61B 17/80* (2006.01)
*A61B 17/86* (2006.01)

(52) U.S. Cl.
CPC ......... *A61B 17/8057* (2013.01); *A61B 17/8605* (2013.01)
USPC ............ 606/291; 606/289; 606/286; 606/283

(58) Field of Classification Search
USPC .................. 606/280, 289, 293, 291, 266, 287
See application file for complete search history.

(56) References Cited

U.S. PATENT DOCUMENTS

| | | |
|---|---|---|
| 300,146 A | 6/1884 | Sinnett |
| 351,751 A | 11/1886 | Douglas |
| 382,670 A | 5/1888 | Trovillion |
| 544,606 A | 8/1895 | Balsley |
| 545,331 A | 8/1895 | Balsley |

(Continued)

FOREIGN PATENT DOCUMENTS

| | | |
|---|---|---|
| AU | 754857 | 11/2002 |
| CA | 2 047 521 | 1/1992 |

(Continued)

OTHER PUBLICATIONS

Machine translation of EP1649819, Dec. 10, 2004.*

(Continued)

*Primary Examiner* — Nicholas Woodall
*Assistant Examiner* — Christine Nelson
(74) *Attorney, Agent, or Firm* — Fish & Richardson P.C.

(57) ABSTRACT

Embodiments of the present invention provide a bone fixation assembly that can provide polyaxial fixation. The polyaxial fixation may be provided by fins that protrude from an opening in a bone plate or fins that protrude from a fastener head.

52 Claims, 13 Drawing Sheets

(56) References Cited

U.S. PATENT DOCUMENTS

| | | |
|---|---|---|
| 565,808 A | 8/1896 | Staples |
| 575,631 A | 1/1897 | Brooks |
| 583,158 A | 5/1897 | Upham |
| 637,990 A | 11/1899 | Hoepner |
| 651,949 A | 6/1900 | Lillie |
| 689,722 A | 12/1901 | Hoover |
| 766,270 A | 8/1904 | Lapham |
| 775,427 A | 11/1904 | Lusted, Sr. |
| 902,040 A | 10/1908 | Wyckoff |
| 1,025,008 A | 4/1912 | Miner |
| 1,105,105 A | 7/1914 | Sherman |
| 1,275,810 A | 8/1918 | White |
| 1,575,149 A | 3/1928 | Craig et al. |
| 1,755,588 A | 4/1930 | Bronk |
| 1,925,385 A | 9/1933 | Humes et al. |
| 2,010,913 A | 8/1935 | Bruce et al. |
| 2,133,859 A | 10/1938 | Hawley et al. |
| 2,152,977 A | 4/1939 | Schindel |
| 2,388,921 A | 11/1945 | Sutter et al. |
| 2,501,978 A | 3/1950 | Wichman |
| 2,524,167 A | 10/1950 | Grande |
| 2,560,912 A | 7/1951 | Aitto |
| 2,667,194 A | 1/1954 | Fischer et al. |
| 2,756,791 A | 7/1956 | Ferrara |
| 3,056,441 A | 10/1962 | Helms |
| 3,279,510 A | 10/1966 | Dreyer et al. |
| 3,347,293 A | 10/1967 | Clark |
| 3,409,058 A | 11/1968 | LaPointe |
| 3,547,114 A | 12/1970 | Haboush |
| 3,552,389 A | 1/1971 | Allgower et al. |
| 3,630,261 A | 12/1971 | Gley |
| 3,662,797 A | 5/1972 | Healis |
| 3,668,972 A | 6/1972 | Allgower et al. |
| 3,716,050 A | 2/1973 | Johnston |
| 3,739,825 A | 6/1973 | Knox |
| 3,741,205 A | 6/1973 | Markolf et al. |
| 3,744,488 A | 7/1973 | Cox |
| 3,779,240 A | 12/1973 | Kondo |
| 3,782,432 A | 1/1974 | Allen |
| 3,866,607 A | 2/1975 | Forsythe et al. |
| 3,906,550 A | 9/1975 | Rostoker et al. |
| 3,935,762 A | 2/1976 | Tudisco |
| RE28,841 E | 6/1976 | Allgower et al. |
| 4,059,102 A | 11/1977 | Devas |
| 4,060,114 A | 11/1977 | Matsushima |
| 4,096,896 A | 6/1978 | Engel |
| 4,219,015 A | 8/1980 | Steinemann |
| 4,246,811 A | 1/1981 | Bondhus et al. |
| 4,263,904 A | 4/1981 | Juder |
| 4,338,926 A | 7/1982 | Kummer et al. |
| 4,364,382 A | 12/1982 | Menen |
| 4,388,921 A | 6/1983 | Sutter et al. |
| 4,408,601 A | 10/1983 | Wenk |
| RE31,628 E | 7/1984 | Allgower et al. |
| 4,484,570 A | 11/1984 | Sutter et al. |
| 4,493,317 A | 1/1985 | Klaue |
| 4,513,744 A | 4/1985 | Klaue |
| 4,535,658 A | 8/1985 | Molinari |
| 4,564,007 A | 1/1986 | Coombs et al. |
| 4,565,193 A | 1/1986 | Streli |
| 4,573,458 A | 3/1986 | Lower |
| 4,683,878 A | 8/1987 | Carter |
| 4,704,929 A | 11/1987 | Osada |
| 4,791,918 A | 12/1988 | Von Hasselbeck |
| 4,794,918 A | 1/1989 | Wolter |
| 4,838,252 A | 6/1989 | Klaue |
| 4,927,421 A | 5/1990 | Goble et al. |
| 4,978,349 A | 12/1990 | Frigg |
| 4,988,350 A | 1/1991 | Herzberg |
| 5,002,544 A | 3/1991 | Klaue et al. |
| 5,006,120 A | 4/1991 | Carter |
| 5,041,114 A | 8/1991 | Chapman et al. |
| 5,053,036 A | 10/1991 | Perrin et al. |
| 5,085,660 A | 2/1992 | Lin |
| 5,129,901 A | 7/1992 | Decoste |
| 5,151,103 A | 9/1992 | Tepic et al. |
| 5,190,544 A | 3/1993 | Chapman et al. |
| 5,192,281 A | 3/1993 | de la Caffiniere |
| 5,197,966 A | 3/1993 | Sommerkamp |
| 5,198,308 A | 3/1993 | Shetty et al. |
| 5,237,893 A | 8/1993 | Ryder et al. |
| 5,259,398 A | 11/1993 | Vrespa |
| 5,269,784 A | 12/1993 | Mast |
| 5,275,601 A | 1/1994 | Gogolewski et al. |
| 5,304,180 A | 4/1994 | Slocum |
| 5,312,410 A | 5/1994 | Miller et al. |
| 5,324,290 A | 6/1994 | Zdeblick et al. |
| 5,324,291 A | 6/1994 | Ries et al. |
| 5,356,410 A | 10/1994 | Pennig |
| 5,360,452 A | 11/1994 | Engelhardt et al. |
| 5,364,398 A | 11/1994 | Chapman et al. |
| 5,364,399 A | 11/1994 | Lowery et al. |
| 5,395,374 A | 3/1995 | Miller et al. |
| 5,415,658 A | 5/1995 | Kilpela et al. |
| 5,423,820 A | 6/1995 | Miller et al. |
| 5,423,826 A | 6/1995 | Coates et al. |
| 5,429,641 A | 7/1995 | Gotfried |
| 5,431,659 A | 7/1995 | Ross, Jr. et al. |
| 5,470,333 A | 11/1995 | Ray |
| 5,474,553 A | 12/1995 | Baumgart |
| 5,487,743 A | 1/1996 | Laurain et al. |
| 5,514,138 A | 5/1996 | McCarthy |
| 5,520,690 A | 5/1996 | Errico et al. |
| 5,522,902 A | 6/1996 | Yuan et al. |
| 5,527,310 A | 6/1996 | Cole et al. |
| 5,531,143 A | 7/1996 | Habermehl et al. |
| 5,531,746 A | 7/1996 | Errico et al. |
| 5,531,748 A | 7/1996 | de la Caffiniere |
| 5,534,032 A | 7/1996 | Hodorek |
| 5,534,932 A | 7/1996 | Van de Waterlaat et al. |
| 5,536,127 A | 7/1996 | Pennig |
| 5,569,253 A | 10/1996 | Farris et al. |
| 5,578,034 A | 11/1996 | Estes |
| 5,591,168 A | 1/1997 | Judet et al. |
| 5,601,553 A | 2/1997 | Trebing et al. |
| 5,607,426 A | 3/1997 | Ralph |
| 5,607,428 A | 3/1997 | Lin |
| 5,643,265 A | 7/1997 | Errico |
| 5,647,873 A | 7/1997 | Errico et al. |
| 5,665,088 A | 9/1997 | Gil et al. |
| 5,665,089 A | 9/1997 | Dall et al. |
| 5,676,667 A | 10/1997 | Hausman |
| 5,702,399 A | 12/1997 | Kilpela et al. |
| 5,709,686 A | 1/1998 | Talos et al. |
| 5,713,900 A | 2/1998 | Benzel et al. |
| 5,725,588 A | 3/1998 | Errico et al. |
| 5,733,287 A | 3/1998 | Tepic et al. |
| 5,735,853 A | 4/1998 | Olerud |
| 5,741,258 A | 4/1998 | Klaue et al. |
| 5,749,872 A | 5/1998 | Kyle et al. |
| 5,769,850 A | 6/1998 | Chin |
| 5,772,662 A | 6/1998 | Chapman et al. |
| 5,776,196 A | 7/1998 | Matsuzaki et al. |
| 5,788,697 A | 8/1998 | Kilpela et al. |
| 5,797,912 A | 8/1998 | Runciman et al. |
| 5,810,823 A | 9/1998 | Klaue et al. |
| 5,824,247 A | 10/1998 | Tunc |
| 5,876,402 A | 3/1999 | Errico |
| 5,888,204 A | 3/1999 | Ralph |
| 5,893,856 A | 4/1999 | Jacob et al. |
| 5,902,305 A | 5/1999 | Beger et al. |
| 5,904,683 A | 5/1999 | Pohndorf |
| 5,904,684 A | 5/1999 | Rooks |
| 5,925,047 A | 7/1999 | Errico et al. |
| 5,935,130 A | 8/1999 | Kipela et al. |
| 5,935,133 A | 8/1999 | Wagner et al. |
| 5,938,664 A | 8/1999 | Winquist et al. |
| 5,954,722 A | 9/1999 | Bono |
| 5,960,681 A | 10/1999 | Anderson et al. |
| 5,961,524 A | 10/1999 | Crombie |
| 5,964,769 A | 10/1999 | Wagner et al. |
| 5,968,046 A | 10/1999 | Castleman |
| 5,968,047 A | 10/1999 | Reed |
| 5,976,141 A | 11/1999 | Haag et al. |

(56) References Cited

U.S. PATENT DOCUMENTS

| | | |
|---|---|---|
| 6,016,727 A | 1/2000 | Morgan |
| 6,019,762 A | 2/2000 | Cole |
| 6,022,352 A | 2/2000 | Vandewalle |
| 6,053,921 A | 4/2000 | Wagner et al. |
| 6,096,040 A | 8/2000 | Esser |
| 6,129,730 A | 10/2000 | Bono et al. |
| 6,176,861 B1 | 1/2001 | Bernstein et al. |
| 6,183,475 B1 | 2/2001 | Lester et al. |
| 6,193,721 B1 | 2/2001 | Michelson |
| 6,206,881 B1 | 3/2001 | Frigg et al. |
| 6,214,049 B1 | 4/2001 | Gayer et al. |
| 6,228,085 B1 | 5/2001 | Theken et al. |
| 6,235,033 B1 | 5/2001 | Brace |
| RE37,249 E | 6/2001 | Leibinger et al. |
| 6,258,092 B1 | 7/2001 | Dall |
| 6,273,889 B1 | 8/2001 | Richelsoph |
| 6,302,001 B1 | 10/2001 | Karle |
| 6,302,883 B1 | 10/2001 | Bono |
| 6,306,136 B1 | 10/2001 | Baccelli |
| 6,306,140 B1 | 10/2001 | Siddiqui |
| 6,309,393 B1 | 10/2001 | Tepic et al. |
| 6,322,562 B1 | 11/2001 | Wolter |
| 6,342,055 B1 | 1/2002 | Eisermann et al. |
| 6,355,041 B1 | 3/2002 | Martin et al. |
| 6,355,043 B1 | 3/2002 | Adam |
| 6,358,250 B1 | 3/2002 | Orbay |
| 6,361,537 B1 | 3/2002 | Anderson |
| 6,364,885 B1 | 4/2002 | Kilpela et al. |
| 6,370,091 B1 | 4/2002 | Kuroda |
| 6,379,359 B1 | 4/2002 | Dahners |
| 6,386,808 B2 | 5/2002 | Fujii |
| 6,391,030 B1 | 5/2002 | Wagner et al. |
| 6,413,259 B1 | 7/2002 | Lyons et al. |
| 6,428,542 B1 | 8/2002 | Michelson |
| 6,436,100 B1 | 8/2002 | Berger |
| 6,440,135 B2 | 8/2002 | Orbay et al. |
| 6,454,769 B2 | 9/2002 | Wagner |
| 6,454,770 B1 | 9/2002 | Klaue |
| 6,468,278 B1 | 10/2002 | Muckter |
| 6,475,218 B2 | 11/2002 | Gournay et al. |
| 6,506,191 B1 | 1/2003 | Joos |
| 6,520,965 B2 | 2/2003 | Chervitz et al. |
| 6,524,238 B2 | 2/2003 | Velikaris et al. |
| 6,527,776 B1 | 3/2003 | Michelson |
| 6,558,387 B2 | 5/2003 | Errico |
| 6,575,975 B2 | 6/2003 | Brace et al. |
| 6,595,993 B2 | 7/2003 | Donno et al. |
| 6,595,994 B2 | 7/2003 | Kilpela et al. |
| 6,605,090 B1 | 8/2003 | Trieu et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,682,531 B2 | 1/2004 | Winquist et al. |
| 6,682,533 B1 | 1/2004 | Dinsdale et al. |
| 6,684,741 B2 | 2/2004 | Blackston |
| 6,689,133 B2 | 2/2004 | Morrison et al. |
| 6,719,759 B2 | 4/2004 | Wagner et al. |
| 6,730,091 B1 | 5/2004 | Pfefferle et al. |
| 6,755,829 B1 | 6/2004 | Bono |
| 6,767,351 B2 | 7/2004 | Orbay et al. |
| 6,780,186 B2 | 8/2004 | Errico |
| 6,821,278 B2 | 11/2004 | Frigg et al. |
| 6,866,665 B2 | 3/2005 | Orbay |
| 6,893,443 B2 | 5/2005 | Frigg et al. |
| 6,893,444 B2 | 5/2005 | Orbay |
| 6,916,320 B2 | 7/2005 | Michelson |
| 6,945,975 B2 | 9/2005 | Dalton |
| 6,955,677 B2 | 10/2005 | Dahners |
| 6,960,213 B2 | 11/2005 | Chervitz et al. |
| 6,969,390 B2 | 11/2005 | Michelson |
| 6,973,860 B2 | 12/2005 | Nish |
| 6,974,461 B1 | 12/2005 | Wolter |
| 6,979,334 B2 | 12/2005 | Dalton |
| 7,073,415 B2 | 7/2006 | Casutt et al. |
| 7,074,221 B2 | 7/2006 | Michelson |
| 7,128,744 B2 | 10/2006 | Weaver et al. |
| 7,172,593 B2 | 2/2007 | Trieu et al. |
| 7,179,260 B2 | 2/2007 | Gerlach et al. |
| 7,230,039 B2 | 6/2007 | Trieu et al. |
| 7,250,053 B2 | 7/2007 | Orbay |
| 7,250,054 B2 | 7/2007 | Allen et al. |
| 7,255,701 B2 | 8/2007 | Allen et al. |
| 7,282,053 B2 | 10/2007 | Orbay |
| 7,294,130 B2 | 11/2007 | Orbay |
| 7,341,589 B2 | 3/2008 | Weaver et al. |
| 7,419,714 B1 | 9/2008 | Magerl et al. |
| 7,695,472 B2 | 4/2010 | Young |
| 7,722,653 B2 | 5/2010 | Young |
| 7,766,948 B1 | 8/2010 | Leung |
| 2001/0037112 A1 | 11/2001 | Brace et al. |
| 2001/0047174 A1 | 11/2001 | Donno et al. |
| 2002/0013587 A1 | 1/2002 | Winquist et al. |
| 2002/0045901 A1 | 4/2002 | Wagner et al. |
| 2002/0058940 A1 | 5/2002 | Frigg et al. |
| 2002/0058943 A1 | 5/2002 | Kilpela et al. |
| 2002/0115742 A1 | 8/2002 | Trieu et al. |
| 2002/0143338 A1 | 10/2002 | Orbay et al. |
| 2002/0161370 A1 | 10/2002 | Frigg et al. |
| 2003/0040749 A1 | 2/2003 | Grabowski et al. |
| 2003/0057590 A1 | 3/2003 | Lohler et al. |
| 2003/0060827 A1 | 3/2003 | Coughln |
| 2003/0105462 A1 | 6/2003 | Haider |
| 2003/0183335 A1 | 10/2003 | Winniczek et al. |
| 2004/0010257 A1 | 1/2004 | Cachia |
| 2004/0030342 A1 | 2/2004 | Trieu et al. |
| 2004/0044345 A1 | 3/2004 | DeMoss et al. |
| 2004/0059334 A1 | 3/2004 | Weaver et al. |
| 2004/0059335 A1 | 3/2004 | Weaver et al. |
| 2004/0073218 A1 | 4/2004 | Dahners |
| 2004/0087954 A1 | 5/2004 | Allen et al. |
| 2004/0097942 A1 | 5/2004 | Allen et al. |
| 2004/0138666 A1 | 7/2004 | Molz, IV et al. |
| 2004/0181228 A1 | 9/2004 | Wagner et al. |
| 2004/0199169 A1 | 10/2004 | Koons et al. |
| 2004/0215195 A1 | 10/2004 | Shipp et al. |
| 2004/0220570 A1 | 11/2004 | Frigg |
| 2004/0236332 A1 | 11/2004 | Frigg |
| 2004/0260306 A1 | 12/2004 | Fallin et al. |
| 2005/0010220 A1 | 1/2005 | Casutt et al. |
| 2005/0010226 A1 | 1/2005 | Grady, Jr. et al. |
| 2005/0027298 A1 | 2/2005 | Michelson |
| 2005/0043736 A1 | 2/2005 | Mathieu et al. |
| 2005/0049593 A1 | 3/2005 | Duong |
| 2005/0070904 A1 | 3/2005 | Gerlach et al. |
| 2005/0080421 A1 | 4/2005 | Weaver |
| 2005/0107796 A1 | 5/2005 | Gerlach et al. |
| 2005/0149026 A1 | 7/2005 | Butler et al. |
| 2005/0165400 A1 | 7/2005 | Fernandez |
| 2005/0192580 A1 | 9/2005 | Dalton |
| 2005/0234457 A1 | 10/2005 | James et al. |
| 2005/0261688 A1 | 11/2005 | Grady, Jr. et al. |
| 2005/0277937 A1 | 12/2005 | Leung et al. |
| 2005/0283154 A1 | 12/2005 | Orbay et al. |
| 2006/0004361 A1 | 1/2006 | Hayeck et al. |
| 2006/0009770 A1 | 1/2006 | Speirs |
| 2006/0009771 A1 | 1/2006 | Orbay et al. |
| 2006/0095040 A1 | 5/2006 | Schlienger et al. |
| 2006/0116678 A1 | 6/2006 | Impellizzeri |
| 2006/0122602 A1 | 6/2006 | Konieczynski et al. |
| 2006/0129148 A1 | 6/2006 | Simmons et al. |
| 2006/0129151 A1 | 6/2006 | Allen et al. |
| 2006/0149265 A1 | 7/2006 | James et al. |
| 2006/0165400 A1 | 7/2006 | Spencer |
| 2006/0167464 A1 | 7/2006 | Allen et al. |
| 2006/0200147 A1 | 9/2006 | Ensign et al. |
| 2006/0235400 A1 | 10/2006 | Schneider |
| 2006/0235410 A1 | 10/2006 | Ralph et al. |
| 2006/0259039 A1 | 11/2006 | Pitkanen et al. |
| 2007/0010817 A1 | 1/2007 | de Coninck |
| 2007/0043366 A1 | 2/2007 | Pfefferle et al. |
| 2007/0093836 A1 | 4/2007 | Derouet |
| 2007/0161995 A1 | 7/2007 | Trautwein et al. |
| 2007/0162016 A1 | 7/2007 | Matityahu |
| 2007/0162020 A1 | 7/2007 | Gerlach et al. |

(56) References Cited

U.S. PATENT DOCUMENTS

| | | |
|---|---|---|
| 2007/0185488 A1 | 8/2007 | Pohjonen et al. |
| 2007/0213828 A1 | 9/2007 | Trieu et al. |
| 2007/0233106 A1 | 10/2007 | Horan et al. |
| 2007/0260244 A1 | 11/2007 | Wolter |
| 2007/0270691 A1 | 11/2007 | Bailey et al. |
| 2007/0270832 A1 | 11/2007 | Moore |
| 2007/0270833 A1 | 11/2007 | Bonutti et al. |
| 2007/0276383 A1 | 11/2007 | Rayhack |
| 2008/0021474 A1 | 1/2008 | Bonutti et al. |
| 2008/0039845 A1 | 2/2008 | Bonutti et al. |
| 2008/0086129 A1 | 4/2008 | Lindemann et al. |
| 2008/0140130 A1 | 6/2008 | Chan et al. |
| 2008/0154367 A1 | 6/2008 | Justis et al. |
| 2008/0154368 A1 | 6/2008 | Justis et al. |
| 2008/0154373 A1 | 6/2008 | Protopsaltis et al. |
| 2008/0167717 A9 | 7/2008 | Trieu et al. |
| 2008/0208259 A1 | 8/2008 | Gilbert et al. |
| 2008/0300637 A1 | 12/2008 | Austin et al. |
| 2009/0024161 A1 | 1/2009 | Bonutti et al. |
| 2009/0076553 A1 | 3/2009 | Wolter |
| 2009/0088807 A1 | 4/2009 | Castaneda et al. |
| 2009/0143824 A1 | 6/2009 | Austin et al. |
| 2009/0149888 A1 | 6/2009 | Abdelgany |
| 2009/0192549 A1 | 7/2009 | Sanders et al. |
| 2009/0312803 A1 | 12/2009 | Austin |
| 2012/0143193 A1 | 6/2012 | Hulliger |

FOREIGN PATENT DOCUMENTS

| | | |
|---|---|---|
| CA | 2 408 327 | 3/2001 |
| CA | 2 536 960 A1 | 3/2005 |
| CH | 611 147 A5 | 5/1979 |
| CN | 1331572 | 1/2002 |
| CN | 1373646 | 10/2002 |
| CN | 1380043 | 11/2002 |
| CN | 1188086 | 2/2005 |
| CN | 101022767 A | 8/2007 |
| DE | 2 602 900 B | 8/1978 |
| DE | 3 513 600 | 10/1986 |
| DE | 3 804 749 | 3/1989 |
| DE | 3 832 343 | 3/1990 |
| DE | 9 000 161 U | 4/1990 |
| DE | 323214 | 1/1992 |
| DE | 4 341 980 B4 | 6/1995 |
| DE | 4 343 117 A1 | 6/1995 |
| DE | 4343117 A1 * | 6/1995 |
| DE | 4 438 261 C1 | 9/1995 |
| DE | 4 438 264 A1 | 3/1996 |
| DE | 19629011 A1 | 1/1998 |
| DE | 198 58 889 A1 | 6/2000 |
| DE | 199 62 317 A1 | 3/2001 |
| DE | 102004035546 | 2/2006 |
| EP | 0 201 024 | 11/1986 |
| EP | 0 207 884 A2 | 1/1987 |
| EP | 0 274 713 A1 | 7/1988 |
| EP | 0 355 035 B1 | 2/1990 |
| EP | 0 486 762 | 5/1992 |
| EP | 0 530 585 | 3/1993 |
| EP | 0 705 572 | 4/1996 |
| EP | 0 468 192 B1 | 9/1996 |
| EP | 0 828 459 B1 | 3/1998 |
| EP | 0 760 632 B1 | 9/2000 |
| EP | 799124 B1 | 8/2001 |
| EP | 1 143 867 | 10/2001 |
| EP | 1 169 971 | 1/2002 |
| EP | 1 211 992 B | 6/2002 |
| EP | 1330209 A2 | 7/2003 |
| EP | 1 364 623 B1 | 11/2003 |
| EP | 1 404 492 A1 | 4/2004 |
| EP | 1 211 994 | 4/2005 |
| EP | 1 211 993 | 10/2005 |
| EP | 1 776 055 A1 | 1/2006 |
| EP | 1 649 819 A1 | 4/2006 |
| EP | 1 658 015 | 5/2006 |
| EP | 1093385 B1 | 12/2006 |
| EP | 1764054 A1 | 3/2007 |
| EP | 1813292 | 8/2007 |
| EP | 1857073 | 11/2007 |
| FR | 2 233 973 | 1/1975 |
| FR | 2 254 298 A1 | 7/1975 |
| FR | 2 405 062 | 5/1979 |
| FR | 2 405 705 | 5/1979 |
| FR | 2 405 706 | 5/1979 |
| FR | 2 496 429 | 6/1982 |
| FR | 2 501 033 B | 10/1985 |
| FR | 2 501 032 B | 2/1987 |
| FR | 2 667 913 | 4/1992 |
| FR | 2 698 261 | 11/1992 |
| FR | 2 706 763 | 12/1994 |
| FR | 2 739 151 | 3/1997 |
| FR | 2 757 370 B | 2/1999 |
| FR | 2 802 082 A1 | 6/2001 |
| FR | 2 831 792 | 5/2003 |
| FR | 2890848 B1 | 11/2007 |
| GB | 580571 | 9/2006 |
| JP | 2003509107 | 3/2003 |
| RU | 2 234 878 C2 | 7/2001 |
| SU | 1279626 A1 | 12/1986 |
| TW | 477687 | 3/2002 |
| WO | WO 8904150 | 5/1989 |
| WO | WO 9007304 | 7/1990 |
| WO | WO 9609014 | 3/1996 |
| WO | WO 9619336 | 6/1996 |
| WO | WO 9625892 | 8/1996 |
| WO | WO 9629948 | 10/1996 |
| WO | WO 9709000 | 3/1997 |
| WO | WO 9834553 | 8/1998 |
| WO | WO 9834556 | 8/1998 |
| WO | WO 9905968 | 2/1999 |
| WO | WO 9925266 | 5/1999 |
| WO | WO 9961081 | 12/1999 |
| WO | WO 0018309 | 4/2000 |
| WO | WO 0019264 | 4/2000 |
| WO | WO 0036984 | 6/2000 |
| WO | WO 0053110 | 9/2000 |
| WO | WO 0053111 | 9/2000 |
| WO | WO0066012 A1 | 11/2000 |
| WO | WO 0119264 | 3/2001 |
| WO | WO 0119267 | 3/2001 |
| WO | WO 0119268 | 3/2001 |
| WO | WO 0178615 | 10/2001 |
| WO | WO 0191660 | 12/2001 |
| WO | WO 0200127 | 1/2002 |
| WO | WO 0234159 | 5/2002 |
| WO | WO 02058574 | 8/2002 |
| WO | WO 02068009 | 9/2002 |
| WO | WO 02096309 | 12/2002 |
| WO | WO 03006210 | 1/2003 |
| WO | WO 03106110 | 12/2003 |
| WO | WO 2004032726 | 4/2004 |
| WO | WO 2004032751 | 4/2004 |
| WO | WO 2004086990 | 10/2004 |
| WO | WO2004089233 A1 | 10/2004 |
| WO | WO 2005018471 | 3/2005 |
| WO | WO 2005018472 | 3/2005 |
| WO | WO 2005032386 | 4/2005 |
| WO | WO2005034722 A2 | 4/2005 |
| WO | WO 2005062902 | 7/2005 |
| WO | WO 2005079685 | 9/2005 |
| WO | WO 2006007965 | 1/2006 |
| WO | WO 2006039636 | 4/2006 |
| WO | WO 2006068775 | 6/2006 |
| WO | WO 2007014192 | 2/2007 |
| WO | WO 2007014279 | 2/2007 |
| WO | WO 2007025520 | 3/2007 |
| WO | WO 2007041686 | 4/2007 |
| WO | WO 2007092869 | 8/2007 |
| WO | WO 2007130840 | 11/2007 |
| WO | WO 2008022136 | 2/2008 |
| WO | WO 2008033742 | 3/2008 |
| WO | WO 2008064211 | 5/2008 |
| WO | WO 2008077137 | 6/2008 |
| WO | WO 2008079846 | 7/2008 |

(56) References Cited

FOREIGN PATENT DOCUMENTS

| WO | WO 2008079864 | 7/2008 |
|---|---|---|
| WO | WO 2008116203 | 9/2008 |
| WO | WO 2009029908 | 3/2009 |

OTHER PUBLICATIONS

Office Action for U.S. Appl. No. 12/484,527, mailed May 18, 2011, 10 pages.

Examiner's First Report on Australian Application No. 2006272646, mailed Mar. 21, 2011, 4 pages.

Office Action for U.S. Appl. No. 12/484,527, mailed Jan. 20, 2011, 9 pages.

NCB® Proximal Humerus Plating System, Surgical Technique, Zimmer, Inc., 2005.

Zimmer® NCB® Plating System, Zimmer, Inc., 2006.

NCB® Distal Femoral Plating System, Surgical Technique, Zimmer, Inc., 2005.

New Trauma Products from AO Development, News—No. 1, 2007.

DePuy Orthopaedics, Inc., entitled, 'Surgical Technique Distal Femoral Locked Plating System,' a Johnson & Johnson company, Polyax Wide Angle Freedom (2005).

Examination Report for corresponding Japanese Application No. 2008-524048, mailed Oct. 25, 2011.

Office Action for U.S. Appl. No. 12/069,331, mailed Aug. 23, 2011, 12 pages.

Australian Office Action in Application No. 2013202741, issued Feb. 3, 2014, 4 pages.

Smith & Nephew Brochure entitled 'Surgical Technique PERI-LOC VLP Variable-Angle Locked Plating System,' pp. 1-32 (Nov. 2007).

Smith & Nephew Brochure entitled 'PERI-LOC VLP Variable-Angle Locked Plating System Distal Tibia Locking Plates,' 04 pages (Oct. 2007).

Smith & Nephew Brochure entitled 'PERI-LOC VLP Variable-Angle Locked Plating System Distal Fibula Locking Plates,' 04 pages (Oct. 2007).

Smith & Nephew Brochure entitled 'PERI-LOC VLP Variable-Angle Locked Plating System Proximal Tibia Locking Plates,' 04 pages (Oct. 2007).

Smith & Nephew Brochure entitled 'PERI-LOC VLP Variable-Angle Locked Plating System Proximal Tibia Variable-Angle Locking Plates,' 04 pages (Nov. 2007).

Smith & Nephew Brochure entitled 'PERI-LOC VLP Variable-Angle Locked Plating System Improved Torsional Fatigue Properties with Thin Locked Versus Non-Locked Plate Constructs for Fixation of Simulated Osteoporotic Distal Fibula Fractures,' 04 pages (Nov. 2007).

DePuy Brochure entitled 'Every Surgeon Has His or Her Own View,' a Johnson & Johnson company, Stryker Numelock II® Polyaxial Locking System, Operative Technique, GTrauma Application, 06 pages (undated).

Winkelstabilitat, litos Unidirectional locking screw technology, Jan. 15, 2008, 5 pages http://www.litos.com/pages/winkelstabilitaet_e.html.

"SMARTLock Locking Screw Technology," http://www.stryker.com/microimplants/products/cmf_smartlock.phn, Mar. 14, 2004.

International Search Report for PCT/US2006/028778, dated Apr. 19, 2007.

"Fracture and Dislocation Compendium," Orthopaedic Trauma Association Committee for Coding and Classification, Journal of Orthopaedic Trauma, vol. 10, Suppl., pp. v-ix, 1996.

"Polyax Wide Angle Freedom Surgical Technique Distal Femoral Locked Plating System," DePuy International Ltd, http://www.rcsed.ac.uk/fellows/Ivanrensburg/classification/surgtech/depuy/.

English Abstract of JP 2002532185, Published Oct. 2, 2002.

English Abstract of ZA 200200992, Published Dec. 18, 2002, Applicant: Synthes AG.

DePuy Orthopaedics, Inc., entitled, 'Surgical Technique Distal Femoral Locked Plating System,' a Johnson & Johnson company, Polyax Wide Angle Freedom (undated).

Office Action for U.S. Appl. No. 13/774,721, mailed Aug. 22, 2013.

Fuchs, S., et al., "Titanium Fixative Plate System with Multidirectional Angular Stability in the Lower Leg and Foot," Trauma Berufskrankh, Mar. 2001(Suppl 4): S447-S453, Springer-Verlag 2001, Certified English Translation Thereof.

Wolter, D., et al., "Titanium Internal Fixator for the Tibia," Trauma Berufskrankh, Mar. 2001(Supp 2): S156-S161, Springer-Verlag 2001, Certified English Translation Thereof.

Jürgens, C., et al., "Special Indications for the Application of the Fixed Angle Internal Fixation in Femur Fractures," Trauma Berufskrankh (1999) 1:387,391, Springer-Verlag 1999, Certified English Translation Thereof.

Fuchs, S., et al., "Clinical Experiences with a New Internal Titanium Fixator for Ventral Spondylodesis of the Cervical Spine," Trauma Berufskrankh (1999) 1:382-386, Springer-Verlag 1999, Certified English Translation Thereof.

Kranz, H.-W., et al., "Internal Titanium Fixation of Tibial Pseudarthrosis, Malalignment, and Fractures," Trauma Berufskrankh (1999) 1:356-360, Springer-Verlag 1999, Certified English Translation Thereof.

Böhmer, G., et al., "TiFix® Angularly Stable Condylar Plate," Trauma Berufskrankh (1999) 1:351-355, Springer-Verlag 1999, Certified English Translation Thereof.

Wolter, D., et al., "Universal Internal Titanium Fixation Device," Trauma Berufskrankh (1999) 1:307-309, Springer-Verlag 1999, Certified English Translation Thereof.

International Preliminary Report on Patentability for International Application No. PCT/US20061028778, mailed Jan. 28, 2008.

Final Office Action for U.S. Appl. No. 12/069,331, mailed Apr. 9, 2012.

Decision of Rejection for Japanese Application No. 2008-0524048, mailed Oct. 30, 2011.

* cited by examiner

SYSTEMS AND METHODS FOR USING POLYAXIAL PLATES

CROSS REFERENCE TO RELATED APPLICATIONS

This application is the U.S. national phase of International Application No. PCT/US2006/028778 filed on Jul. 25, 2006 and published in English on Feb. 1, 2007 as International Publication No. WO 2007/014192 A2, which application claims the benefit of U.S. Provisional Application Ser. No. 60/702,231 filed Jul. 25, 2005 titled "Locking Screw," the entire contents of which are hereby incorporated by reference.

BACKGROUND OF THE INVENTION

The present invention relates generally to orthopedic fixation devices and bone plating systems for fracture fixation, and particularly to systems and methods for using bone plates that provide polyaxial fixation of fasteners.

Bone fractures are often repaired by securing a bone plate across the fracture. Depending upon which bone is to be treated, the bone plate may be straight or curved to match the contour of the bone for which it is designed. Bone plates may also be provided in many shapes and sizes. In cases where a bone is severely comminuted or if bone segments are missing, the use of bone plate and screw systems promotes healing of the fracture by providing a rigid fixation or support structure between the bone and the plate.

Bone plates may be secured to the bone in a number of ways. An existing solution is a plate and screw system where the screws are locked in the plate. A bone screw is threaded through an opening in the plate and into the bone. The screw is then secured to the bone plate via threads in the screw head that cooperate with threaded openings in the bone plate. This secures the plate with respect to the bone and provides rigid fixation because the relationship between the plate and screw (s) is fixed. Because the head of the locking screw interdigitates with threads in the plate, the plate and screws(s) form one stable system, and the stability of the fracture can be dependent upon the stiffness of the construct. Locking a screw into the plate can achieve angular and axial stability and eliminate the possibility for the screw to toggle, slide, or be dislodged, reducing the risk of postoperative loss of reduction.

However, although may reduce the incidence of loosening, they provide only one fixed angle relationship between the plate and the screw(s). They have a limited insertion angle because the threads of the head mate with the threads of the hole in one way only. The longitudinal axis of the screw lines up with the central axis of the hole, and no angular variation is allowed. In short, locking screws are unidirectional, limiting their use in some instances.

For example, when treating a severe fracture, fragments may be shattered and in irregular positions. Although a surgeon may wish to obtain the benefits of a locking screw and bone plate used together, the angle at which the locking screw extends from the plate at a certain opening may not be the angle that would allow the surgeon to "grab" (or seize, or otherwise secure) the desired, random bone fragment. In this case, the surgeon may need to secure the plate to the bone somewhere else, or use a non-locking screw. Although non-locking screws do not lock into the plate, they can be inserted at various angles.

Specifically, non-locking screws are secured into bone in the same way that locking screws are, but they are not secured to the plate. Their heads are typically rounded where they contact the bone plate. Thus, one advantage of non-locking screws is that they can be inserted at various angles because they are not limited by the thread-to-thread contact of locking screws with the bone plate. However, if the surgeon desires the rigid stable construct of a locking screw and plate, the use of a non-locking screw to obtain the desired angular orientation is not necessarily optimal.

There have been bone plating systems developed that provide the surgeon with the option of choosing a non-locking or a locking screw. In some embodiments, these systems provide plates with some threaded holes (that may receive with either locking screws or non-locking screws) and some non-threaded holes (for non-locking screws). There are also systems that provide partially threaded slots to allow either non-locking or locking screws to be used together. Such combination slots provide surgeons with the intraoperative choice about whether to use the plate with locking screws, non-locking screws, or with a combination of both. These combination slots typically have a partially threaded opening that can receive either a compression screw or a locking screw. However, because these combination slots are only partially threaded, the locking screw(s) may not be able to maintain the fixed angular relationship between the screw(s) and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intraoperative plate orientation. Moreover, the locking screw can still only be inserted at a single angle—the predetermined angle defined by the manufacturer.

Additionally, current bone plate and screw systems still limit a surgeon's ability to both (a) lock a fastener with respect to the bone plate, but still (b) allow the fastener to extend from the bone plate at various angles. Locking screws lock into the plate, but only in a single angular configuration, and non-locking screws allow various angle configurations, but they do not provide a stable construct with the plate. Accordingly, none of these options allow a surgeon to capture bone fragments that do not fall in line with the axis of the opening provided on the plate in a rigid fashion. An example of this problem is shown in FIG. 21. Thus, currently available options can still lead to malalignment and poor clinical results.

There have, however, been some attempts to provide polyaxial locking systems. For example, one effort includes providing holes that accept fixed angle locking pegs and multidirectional locking pegs, with a threaded cap inserted over the multidirectional peg to hold it into place. Such a system can be cumbersome to use because although the multidirectional peg can be inserted at any angle, the surgeon then needs to thread a small cap onto the top of the peg head and into the plate, requiring an extra step, extra time, and extra instrumentation. Such systems also fail to allow the use of non-locking members in conjunction with the locking and multidirectional pegs.

Other systems that have attempted to offer polyaxial fixation include providing a bone plate with inserts at the hole peripheries made out of a deformable material, with the remaining part of the plate made of titanium. The plate is manufactured and the inserts are then pushed into the hole peripheries and engaged in place by deformation and pressure. When screws are inserted, the inserts deform and are compressed between the edges of the holes of the plate, which holds the screws and inserts in place. Challenges with such systems are that they cannot be used with non-locking screws, the inserts do not have the strength to receive and hold a regular locking screws, (i.e., they do not provide the surgeon with options), and plates with deformable inserts are more expensive to manufacture than regular bone plates. Other attempts have failed to provide adequate locking mechanisms.

Another attempt at polyaxial fixation includes a plate with holes that have an internal jacket with recesses that extend away from the axis of the hole or into the internal jacket surface. This attempt is described in International Application WO 2005/018472, titled Bone Plate. The internal jacket surface of the plate described in that application is threaded or has ribs or protuberances. A bone screw is intended to be pulled into the hole of the plate by the internal jacket surface. If the bone screw head is threaded, when the screw in inclined, the threaded head is intended to "jump over" the pitches of the threads in the hole of the plate interrupted by the recesses, without "cutting through" them. The goal of the invention is provide a bone plate that can have bone screws introduced at an angle that is different from the specified axis of the hole and secured into position.

However, some of the problems encountered by this attempted solution are that (1) threaded openings in bone plates typically require the plate to be of a certain thickness and thus, do not lend themselves to use with a thin plate, (2) threaded openings can be difficult and more expensive to manufacture than non-threaded openings in a bone plate, and (3) threaded openings can take more effort in use because the surgeon needs to have the appropriate alignment for use. Moreover, the threads of this application are short because they are interrupted by the recesses so it is likely that a fastener will not actually "grab" the threads to get good engagement.

Accordingly, there exists a need for an improved bone plating system that overcomes the deficiencies of the prior art. There is a need for a system that provides a stable connection between a bone and a bone plate using a fastener that permits different angles to be obtained between the bone plate and the fastener, while the fastener also locks into the bone plate. This would allow surgeons to capture random bone fragments that are in irregular positions, for example, in cases of severe fractures with highly fragmented bone fragments. In these and other cases, it would be advantageous to provide a fastener and plate system that allows the surgeon to choose the angle at which the screw is inserted through, and rigidly affixed in, an opening of the plate.

Such an improvement would allow a surgeon to direct the fastener toward bone fragments that are not necessarily located directly beneath the opening in the plate. It would also provide flexibility in the placement of the plate in relation to the bone fracture. Allowing surgeons to choose the angle at which the fastener is inserted into the plate would lead to better tailoring of the system to the specific nature of the bone fracture to be treated. It would also allow surgeons to adjust their strategy as necessary after the surgical site has been accessed, but prior to insertion of the fastener into bone material. Additionally, in situations where it is desirable to insert a fastener into a plate in a coaxial or polyaxial direction, the embodiments described herein would provide such a secure fit.

BRIEF SUMMARY OF THE INVENTION

Embodiments of the present invention relate to a bone fixation assembly that can provide polyaxial fixation. The polyaxial fixation may be provided by fins that protrude from an opening in a bone plate or fins that protrude from a fastener head. For example, according to one aspect of the invention, there may be provided a polyaxial bone fixation assembly comprising
  (a) a bone plate comprising a lower surface, an upper surface and at least one opening extending from the lower surface to the upper surface;
  (b) a fastener that is insertable through the opening; and
  (c) at least one member of co-operation between the opening and the fastener comprising a plurality of protruding fins located within the opening or on the fastener.

In a specific aspect or embodiment, the opening has a non-threaded inner surface and wherein the fins are located on the inner surface.

Further embodiments have fins that are a series of concavely indented, inwardly protruding fins that are adapted to secure a threaded head of a fastener in place at varying angles.

According to a further embodiment, the opening is further defined by a round circumference at the upper surface and a jagged circumference formed by the protruding fins at the lower surface.

According to a further embodiment, the protruding fins form a concave portion of the inner surface.

According to an even further embodiment, the protruding fins have bases that meet the inner surface in substantially the same plane.

According to another embodiment, the fastener has a threaded head adapted to engage with the protruding fins.

Another embodiment provides fins that have a tapered shape, a straight shape, a rectangular shape, or a triangular shape.

A further embodiment provides a bone plate with the opening located on the head.

In further specific aspect or embodiment, the fastener has a head with fins, wherein the fins are adapted to cooperate with threads in a bone plate.

According to another embodiment, the fins are provided in more than one layer.

Another embodiment provides the opening in the bone plate with one or more rectangular threads.

In a further embodiment, the fins are trapezoidally-shaped, rounded, oval, rectangular, curved, rhomboid, diamond-shaped, or triangular. The fins may also have the edges of fins taper inwardly, outwardly, or are about parallel with one another.

According to a further embodiment, the bone plate is adapted to contact a femur, a distal tibia, a proximal tibia, a proximal humerus, a distal humerus, a clavicle, a fibula, an ulna, a radius, bones of the foot, or bones of the hand.

Further embodiments have a bone plate with one or more of the following features:
  (a) contoured, straight, or flat;
  (b) a head portion that is contoured to match a particular bone surface;
  (c) a head that flares out to form an L-shape, T-shape, or Y-shape; and
  (d) any combination thereof.

Other embodiments provide the bone plate with one or more of the follow openings:
  (a) a threaded opening;
  (b) a non-threaded opening;
  (c) an opening adapted to receive locking or non-locking fasteners;
  (d) a combination slot; or;
  (e) any combination thereof.

Other aspects of the invention also provide methods for securing a bone plate to a bone using polyaxial fixation. For example, one aspect provides a method for securing a bone plate to a bone using polyaxial fixation, comprising:
- (a) providing a bone plate comprising a lower surface, an upper surface, and at least one opening extending from the lower surface to the upper surface, the opening having a non-threaded inner surface with one or more protruding fins located on the inner surface;
- (b) providing a fastener having a shaft and a head, the head having at least one set of threads adapted to cooperate with the protruding fins;
- (c) inserting the fastener into the opening of the bone plate and allowing the at least one set of threads to engage the fins of the plate; and
- (d) securing the bone plate to bone.

Another aspect provides a method for securing a bone plate to a bone using polyaxial fixation, comprising:
- (a) providing a bone plate comprising a lower surface, an upper surface, and at least one opening extending from the lower surface to the upper surface; the opening having one or more threads;
- (b) providing a fastener having a shaft and a head, the head having at least one set of fins adapted to cooperate with threads of the plate;
- (c) inserting the fastener into the opening of the bone plate and allowing the one or threads to engage the fins of the fastener head; and
- (d) securing the bone plate to bone.

Embodiments of the above aspects include using polyaxial fixation to draw a bone fragment into alignment.

Another embodiment includes inserting a locking screw or a non-locking screw into the bone plate.

"Embodiment" as used herein can be considered to mean an aspect or object of the invention, and vice versa.

DETAILED DESCRIPTION OF THE INVENTION

Figure 1:
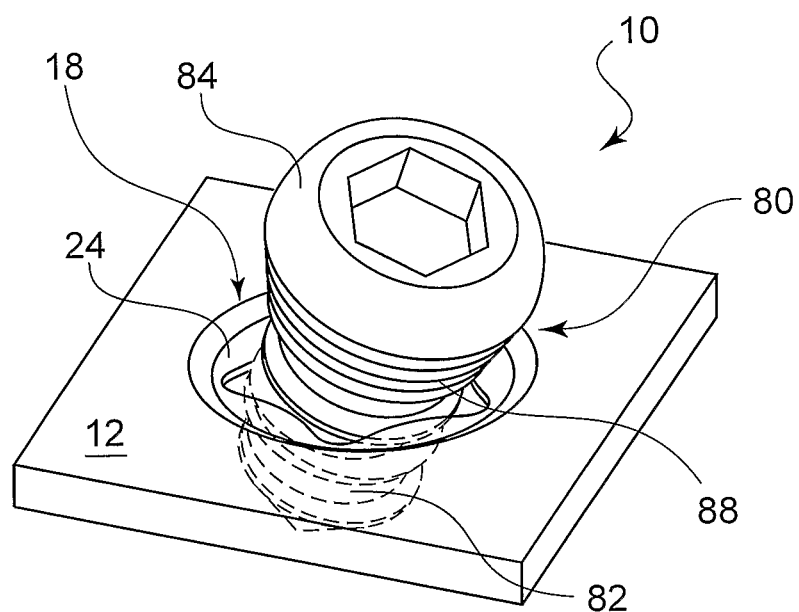
FIG. 1 shows a perspective view of a bone plate having fins according to one embodiment of the invention with a fastener inserted therein.

Embodiments of the present invention provide a bone fixation assembly that can accept and fix fasteners at a plurality of angles. A specific embodiment of a bone fixation assembly 10 is shown as a bone plate 12 and fastener 80 in FIG. 1. As shown in more detail in FIGS. 2-4, bone plate 12 has a lower surface 14 and an upper surface 16 and one or more openings 18 that extend from the lower surface 14 to the upper surface 16.

Figure 11:
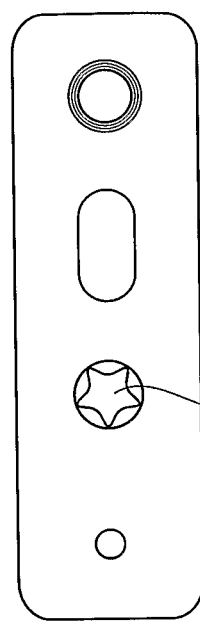
FIGS. 11-15 show alternate shapes and types of bone plates that may be used with various embodiments of this invention.

The embodiments described herein may be used in connection with any type of bone plate, non-limiting examples of which are shown in FIGS. 11-15. Plate 12 may be adapted to contact one or more of a femur, a distal tibia, a proximal tibia, a proximal humerus, a distal humerus, a clavicle, a fibula, an ulna, a radius, bones of the foot, or bones of the hand. The bone plate may be curved, contoured, straight, or flat. It may be a periarticular plate or a straight plate. An example of a straight plate is shown in FIG. 11. Plate 12 may have a head portion that is contoured to match a particular bone surface, such as a metaphysis or diaphysis, flares out from the shaft portion, that forms an L-shape, T-shape, Y-shape, with the shaft portion, or that forms any other appropriate shape to fit the bone to be treated. An example of a T-shaped plate is shown in FIGS. 12-15, the openings on the plates in those figures are described in more detail below.

Bone plate 12 may be comprised of titanium, stainless steel, cobalt chrome, plastic—such as polyetheretherketone (PEEK), polyethylene, ultra high molecular weight polyethylene (UHMWPE), or a carbon composite—resorbable polylactic acid (PLA), polyglycolic acid (PGA), combinations or alloys of such materials or any other appropriate material that has sufficient strength to be secured to and hold bone, while also having sufficient biocompatibility to be implanted into a body. Although the above list of materials includes many typical materials out of which bone plates are made, it should be understood that bone plates comprised of any appropriate material are within the scope of this invention.

Figure 5:
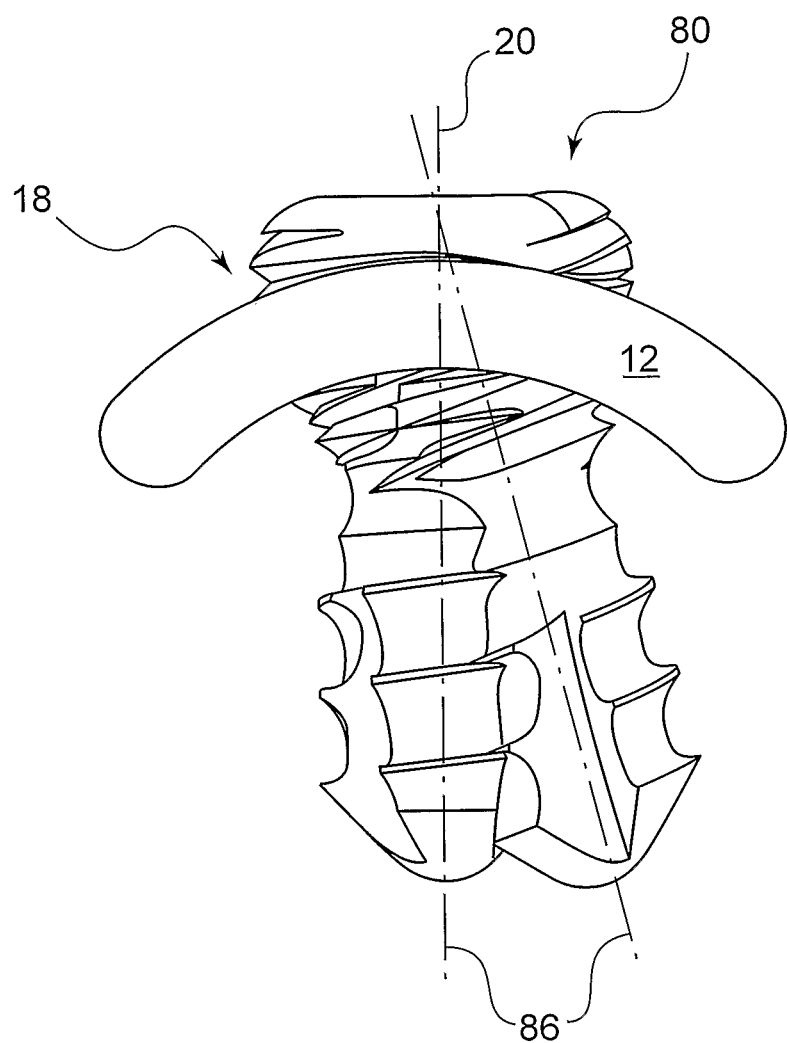
FIG. 5 shows a side perspective view of a bone plate with fasteners inserted therein to illustrate a few of the multiple angles at which the plate can receive a fastener.
Figure 6:
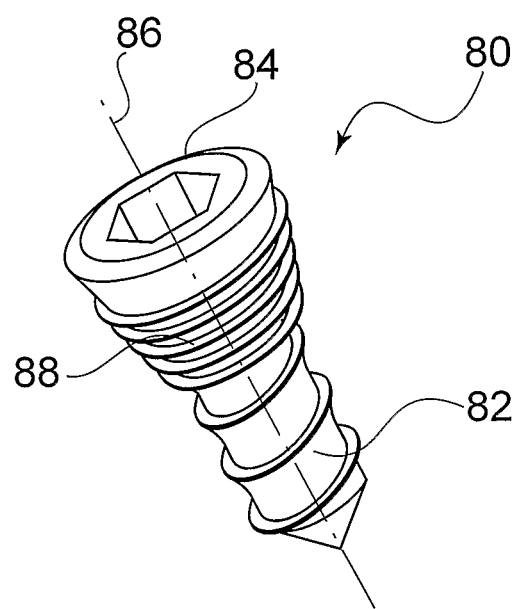
FIG. 6 shows an example of a fastener for use with various bone plates described herein.

Opening 18 of plate 12 is shown having a central axis 20, and it is adapted to receive a fastener. The fastener may be any typical, standard locking fastener or a non-locking fastener, although the embodiments described herein are intended for particular use with locking fasteners that have a series of threads on their heads. FIGS. 5-6 show examples of fastener 80 that may be used in accordance with embodiments of this invention. As shown specifically in FIG. 6, fastener 80 has a shaft 82 and a head 84. Shaft 82 may be threaded or otherwise configured to engage bone. It may be fully threaded, partially threaded, comprise a helical blade, and/or may comprise one or more tacks, deployable talons, expanding elements, or so forth. Any feature that allows shaft 82 to engage bone is considered within the scope of this invention and may be referred to generally as a "threaded shaft" for the sake of convenience. It is also possible, however, that shaft 82 is not threaded, so that fastener 80 takes the form of a peg or a pin. This alternative embodiment may be preferred in certain procedures where, for instance, the main goal is to prevent tilting of a bone segment, or in procedures where there is no concern of fastener 80 pulling out from the bone and hence no need for shaft 82 to be threaded or otherwise configured to engage bone. For the sake of reference, shaft 82 is also shown having a longitudinal axis 86. The end of shaft 82 may be a self-tapping or self-drilling tip, as shown in more detail in FIG. 5.

The head 84 of fastener 80 preferably has at least one set of threads 88. Threads 88 are typically any standard-type thread. For example, the threads 88 may be a continuous ridge or a non-continuous ridge. It may comprise a portion of a revolution, one complete revolution, multiple revolutions, a single lead, or multiple leads, or any other threads known in the art. Additionally or alternatively, head 84 of fastener 80 may include any other surface that will engage with and seat within specific features of plate (described further below). For example, head 84 may have a series of dimples, ridges, bumps, textured areas, or any other surface that can secure fastener 80 as described herein. As will be described in more detail below, threads 88 of head are adapted to engage, associate with, or otherwise cooperate with fins 24 of opening 18. In short, any type of threaded fastener head is intended for use with various embodiments of this invention.

Figure 2:
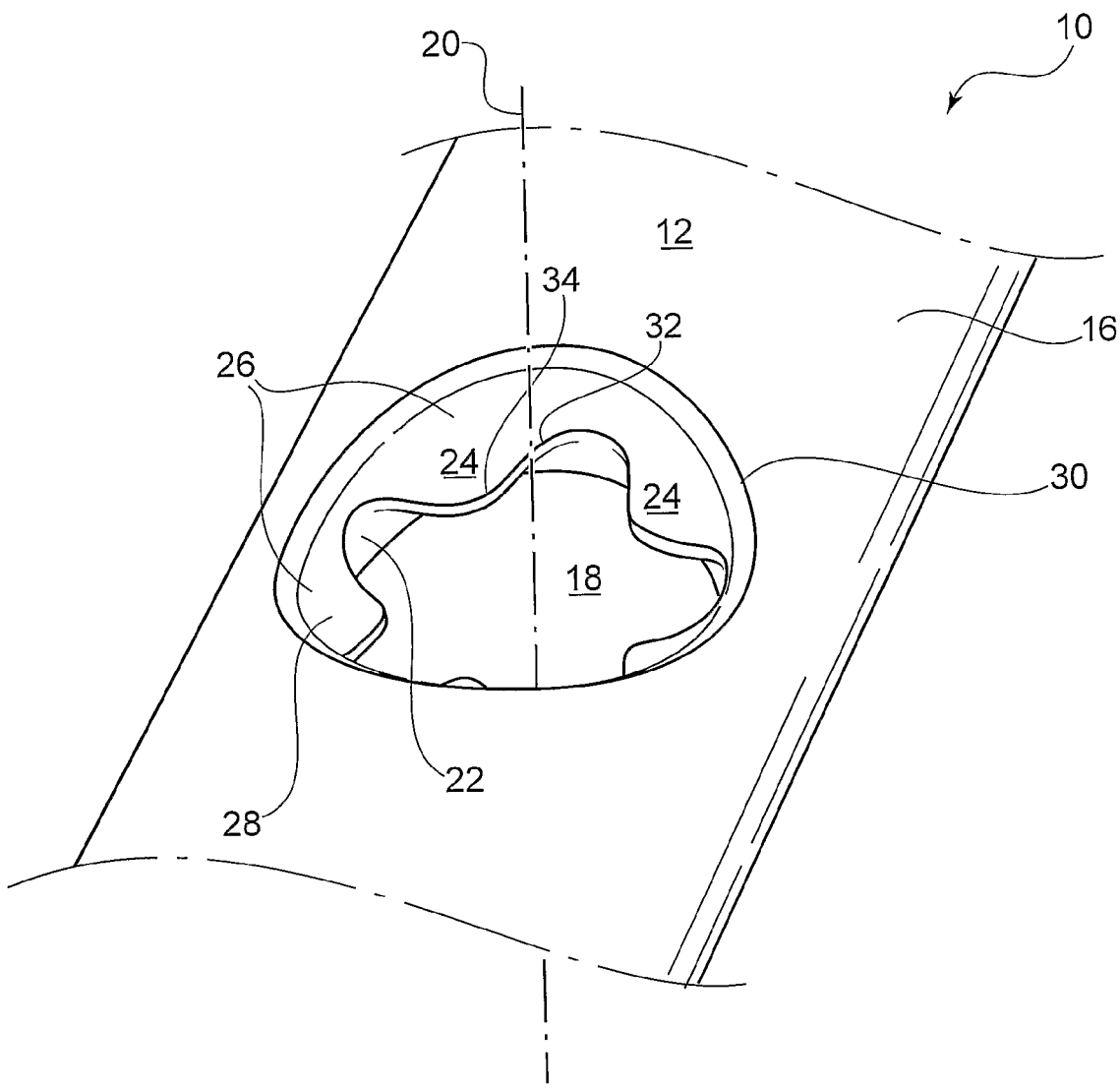
FIG. 2 shows a top perspective view of an opening in a bone plate according to one embodiment of the invention.
Figure 3:
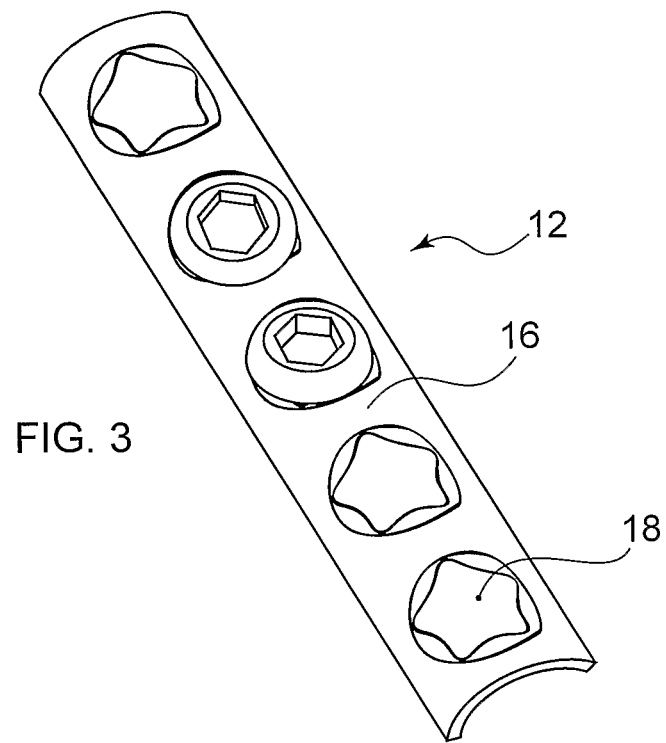
FIG. 3 shows a top view of a bone plate having multiple openings, with a fastener inserted therein.

Referring to FIG. 2, it can be seen that the embodiment shown has an opening 18 with an inner surface 22 that is defined by a series of concavely indented, inwardly protruding fins 24. Fins 24 extend into opening 18 toward central axis 20. The bases 26 of fins 24 form a concave portion 28 at or near a round circumference 30 of upper surface 16. (The term "round" circumference is intended to refer to any round shape, such as a circle, an oval, an egg-shaped circumference, or any other opening shaped to receive the head of a fastener 80.) The bases 26 of the fins 24 may all meet in substantially the same plane and then angle downwardly and inwardly at a similar angle or slope.

It bears noting that the concave portion 28 is smooth and non-threaded. In fact, there are not any threads on concave portion 28 or anywhere on inner surface 22 of opening 18. The lack of threads helps ease the manufacturing of plate 12, and allows plate be manufactured as thinly as desired.

For example, the thickness of plate 12 and the dimensions of fins 24 are typically dependent upon the pitch and threads of fastener 80. For example, a larger plate 12 for use with a larger fastener (e.g., for use on a femur bone) will likely be thicker and will have larger and thicker fins than a smaller plate (e.g., for use on a smaller bone). In specific embodiments, the fins 24 are particularly thin so that they can be moved up or down and deformed upon pressure. In some embodiments, the fins may be pressed toward the edges of the plate opening. A non-limiting exemplary range of thicknesses for fins may be from about 0.5 mm to about 5 mm, although larger and smaller sizes are possible. In theory, the fins 24 are intended to fit between crimps on the threadform of fastener 80, as shown in FIG. 1.

Providing a non-threaded inner surface 22 also allows the fastener 80 to be inserted into opening 18 at any desired angle, because there are not any threads to interfere with the desired angle, as illustrated by FIG. 5. The fins 24 are intended to slightly bend or deform in order to secure the fastener 80 in place in opening 18. Fins 24 actually engage threads 88 or other surface of fastener 10.

Figure 8:
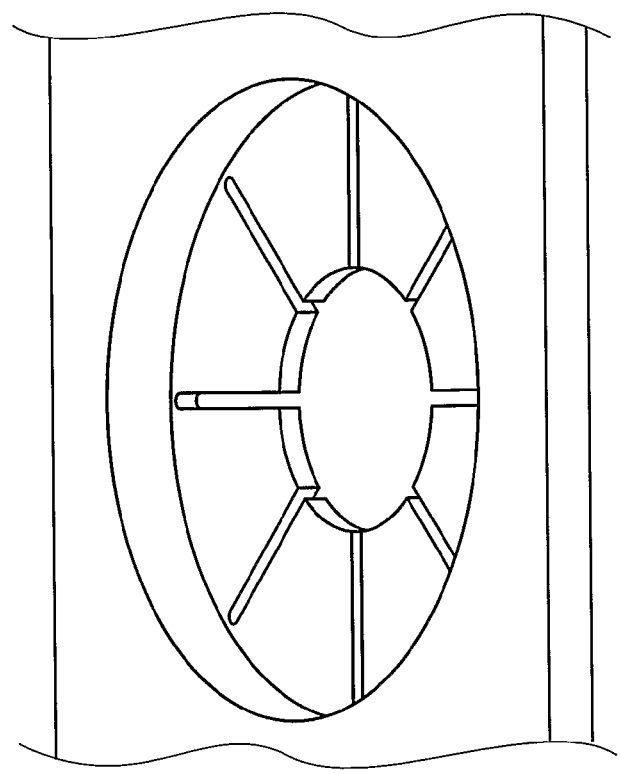
FIG. 8 shows a perspective view of the bone plate of FIG. 7.
Figure 7:
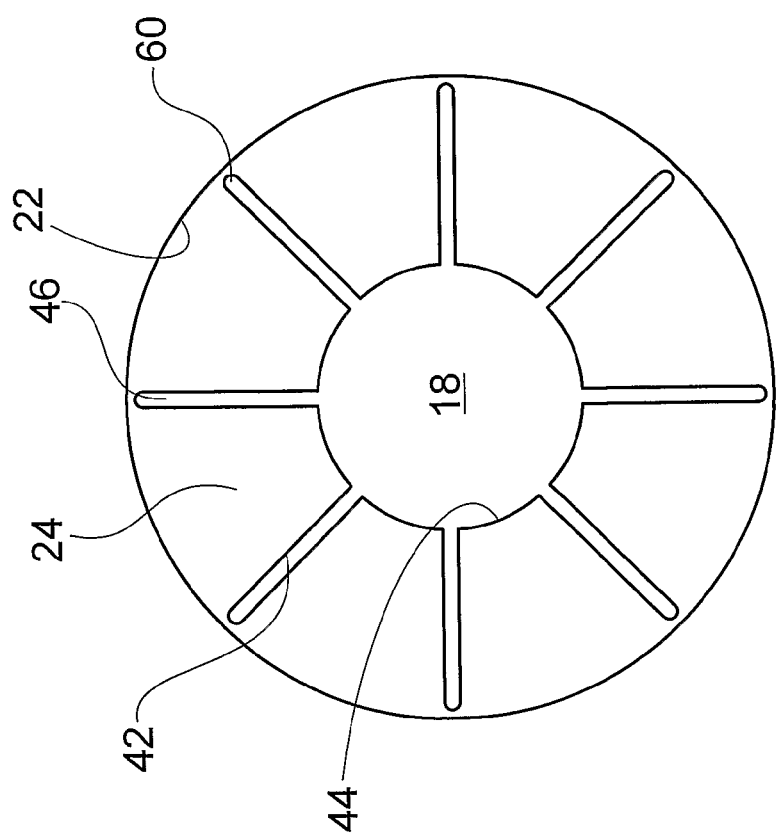
FIG. 7 shows a top plan view of an alternate embodiment of an opening in a bone plate.

Referring back to FIG. 2, in the embodiment shown, as fins 24 extend toward central axis 20, they taper to form tapered sides 32. The fins end at rounded tip 34, although tips 34 can be pointed, square, rectangular, or any other appropriate configuration. For example, as shown in FIGS. 7 and 8, fins 24 may have straight edges or sides 42 and straight ends 44. This embodiment shows fins 24 that are partially rectangular-shaped. The openings 46 between fins 24 are slit-shaped.

Figure 10:
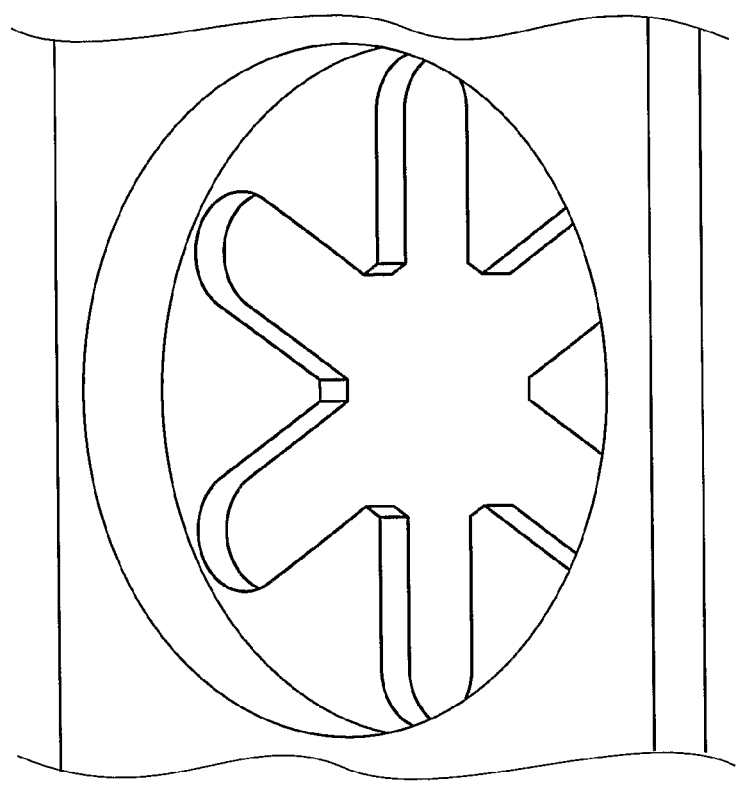
FIG. 10 shows a perspective view of the bone plate of FIG. 9.
Figure 9:
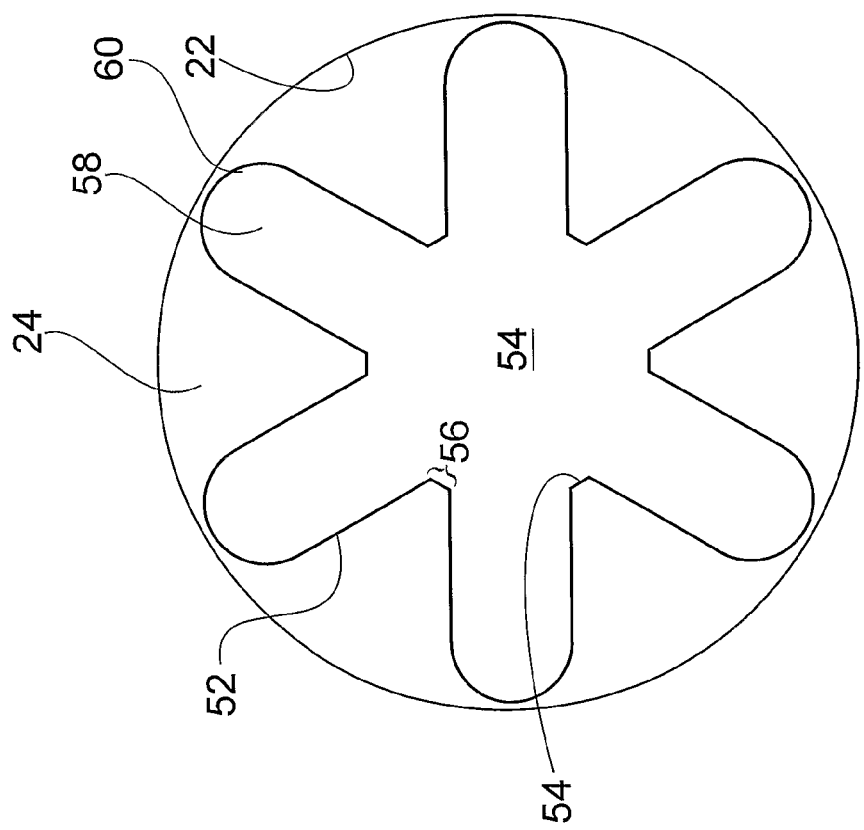
FIG. 9 shows a top plan view of a further embodiment of an opening in a bone plate.

An alternate embodiment is shown in FIGS. 9 and 10, which illustrate fins 24 with a more triangular shape. In this embodiment, fins 24 are shown having sides 52 that taper inwardly and edges 54 that are flat and small, forming the apex area 56 where sides 52 come to an end. Openings 58 between fins 24 are more elongated than openings 46. Both sets of openings 46, 58 in these alternate embodiments are shown having rounded backs 60, where they meet inner surface 22 of opening 18. It should be understood however, that these are merely examples of fin 24 shapes and openings 46, 58 and that any appropriate shapes are possible and considered within the scope of this invention. Non-limiting examples include trapezoidal, square, round, circular, triangular (with a pointed tip instead of apex area 56), and any other possible option.

Figure 4:
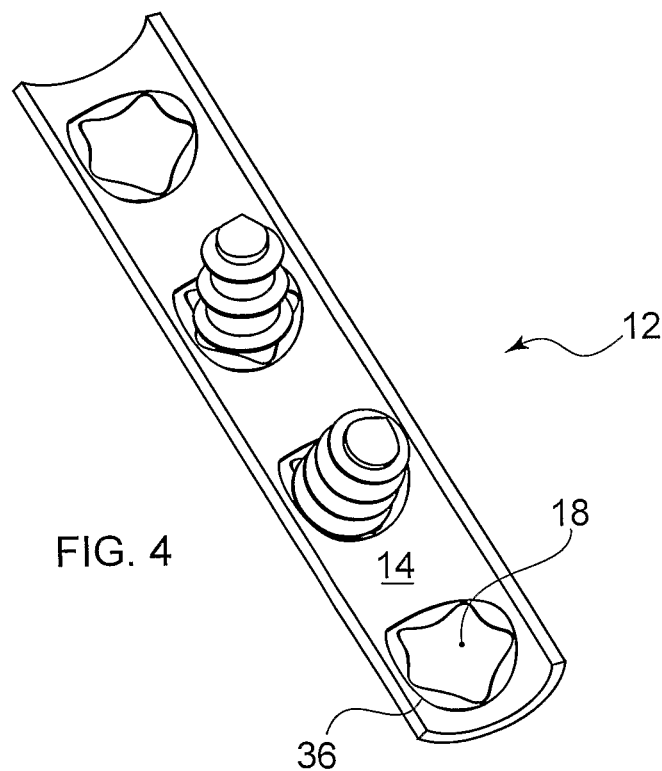
FIG. 4 shows an underneath view of the bone plate of FIG. 3.

As shown in FIG. 4, a second circumference 36 at the lower or underneath surface 14 of plate 12 may appear to be more jagged than the round circumference 30 at the upper surface 16 due to the fins 24 forming a portion of lower surface 14. The circumference can appear almost "flower-like"—each fin 24 appears to form a petal of the circumference. Alternatively, for the embodiments of FIGS. 7-10, the second circumference will appear similar to the shape created by fins 24.

Although the figures show an opening 18 with about five to eight fins 24, it should be understood that any number of fins 24 is considered within the scope of this invention. For example, there may be two or three fins, or ten or twenty or more fins 24, depending upon the plate for which the opening 18 is intended for use.

The primary purpose of fins 24 is to grasp one or more threads 88 of a threaded head fastener in order to secure the fastener in place in the bone plate 12, but at any angle. For example, as opposed to threaded openings (which engage the threads of the head of the fastener in one way only, limiting the surgeon's ability to angle the fastener as desired), the fins 24 of this embodiment are still intended to secure the threads of the head of fastener in place, but at any angle. As the fastener is inserted, its threads start to engage the fins 24, as shown in FIG. 1. As discussed above, the fins 24 may be very thin so that as the head threads 88 start to grab fins 24, the fins 24 may move up or down as appropriate to engage the threads 88 and secure the fastener 80. In short, the threads 88 engage fins 24 (or fit in between fins 24). In most cases, this movement of fins 24 is a permanent deformation, so that the fins cannot flex back and allow the fastener to work its way out.

Figure 12:
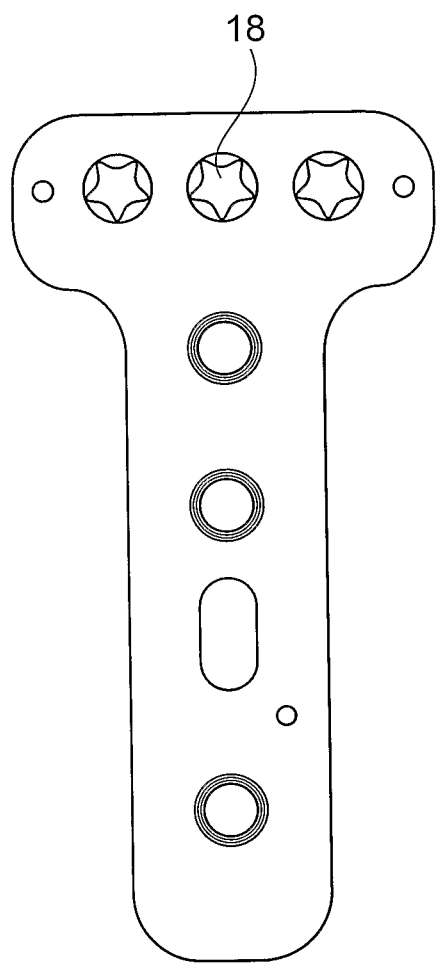
Figure 15:
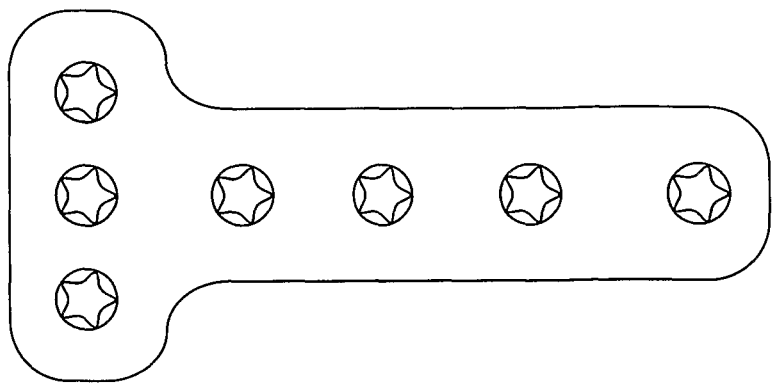
Figure 14:
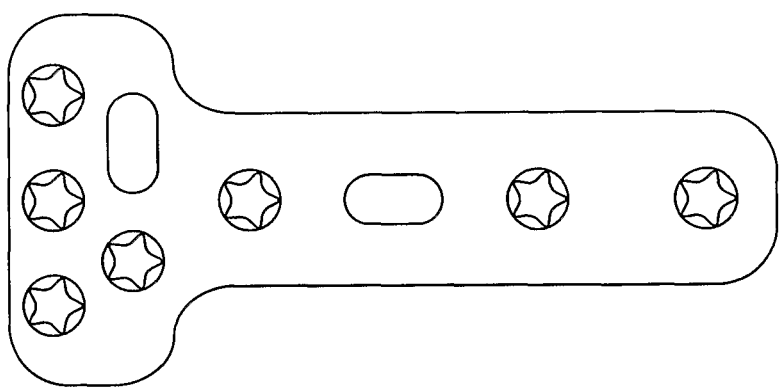
Figure 13:
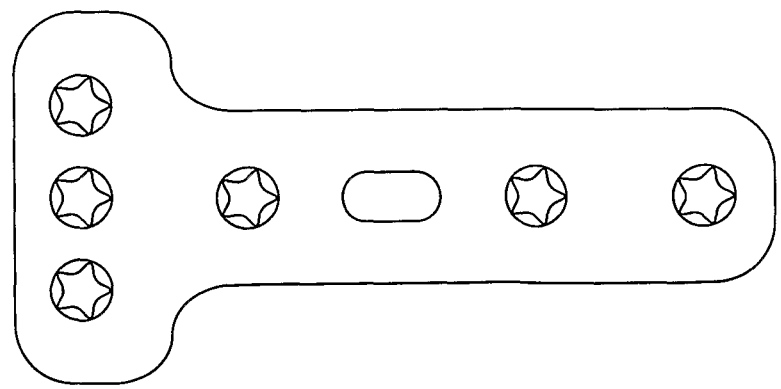

As discussed above, finned openings 18 may be provided on all types of bone plates, examples of which are shown in FIGS. 11-15. FIG. 11 shows a specific example of an opening 18 with fins 24 (referred to as a finned opening 18), a smooth opening 60, a threaded opening 62, and a provisional pin opening 64. Other options are holes that can be used with either a threaded or non-threaded fastener, as well as combination slots. It should be understood that these various types of openings may be used on any types of bone plates, in any combination and in any size, examples of which are shown in FIGS. 12-15. FIG. 12 shows a plurality of finned openings 18 in the head 70 of bone plate 12. This may help achieve better fixation of a fractured bone, because the fastener can be inserted at various angles to capture "renegade" or random bone fragments that have split from the bone during fracture, but still secure the bone fragments to the plate. For example, if a wrist bone is broken, there will be numerous fragments that may shatter in various directions. The plates 12 with finned openings 18 described herein can be used to place a fastener 8—at various angles in order to capture the renegade fragments that would otherwise not be secured to a bone plate using only a locking or a non-locking fastener. It should additionally be understood that other types of openings (in addition to or instead of finned openings 18) may be present in the head 70, as well as elsewhere on plate 12.

As previously mentioned, fastener 80 may be any typical fastener, made out of any appropriate material. It will typically have a bore for receiving a driver in order to secure fastener into bone and into plate 12. The receiving bore may be any size and shape, for example, it may have a hexagonal configuration to receive a corresponding hexagonal driver, a Phillips screw head, a flat-head, a star configuration, Torx, or any other appropriate configuration that can cooperate with a driver to place fastener.

Turning now to the methods of implantation, the surgeon accesses the surgical site of interest, which can be an internal site at which a bone fracture is located that requires stabilization to ensure proper healing. The fracture may be reduced with conventional forceps and guides (which are known to those in the art), and a bone plate of appropriate size and shape is placed over the fracture site. In some instances, the bone plate may be temporarily secured to the bone using provisional fixation pins. In the bone plates shown in FIGS. 11 and 12, provisional fixation pins may be used through either the provisional pin openings, or any other opening (threaded or non-threaded or finned) in the plate. Provisional fixation provides for temporarily securing the bone plate to the bone before placing fixation screws through the bone plate, so that one can be certain the bone plate is properly positioned before placing bone screws for permanent fixation of the bone plate to the bone. Moreover, with provisional fixation, x-rays can be taken of the bone plate/construct without excess instruments in the field of view.

Once the plate 12 is secured at a desired location in relation to the fracture (typically using one or more provisional fixation pins, although any other appropriate method may be used), the surgeon then identifies an insertion angle, or the direction along which fastener 80 is to be inserted through a selected opening 18 and driven into bone material. If bone plate 12 includes more than one opening, as shown in the figures, the surgeon also selects the specific opening to be used. After selecting the desired insertion angle and opening, the surgeon inserts shaft fastener 80 through opening 18 until the tip contacts bone material. In some cases, a hole may need to be drilled or tapped into the bone along the insertion angle to facilitate the initial tapping or insertion of fastener 80. The surgeon then uses an appropriate driving tool in the receiving bore of head 84 to manipulate the fastener 80 into place.

Because fastener 10 may be inserted at angles other than the aligned with the central axis 20 of the opening 18, as shown in FIG. 5, fastener 80 may be used to grab or secure bone fragments that are out of line with the traditional angle at which a locking screw would normally be inserted. The surgeon may need to toggle or maneuver the fastener 80 in order to secure and draw in displaced bone fragments.

Once the bone fragment is secured, the fastener 80 is ready to be secured to the plate 12. As fastener 80 is driven further into bone, it is also drawn further into plate 12. As threads 88 of fastener head 84 begin to contact fins 24, the fins are allowed to engage within the threads to hold the fastener 80 in place in the desired angle, even angles that are other than in line with the central axis 20. The action of engagement between fins 24 and threads 88 rigidly affixes fastener 80 to the bone plate 12 at the desired insertion angle. In some embodiments, the surgeon may then use traditional locking and/or non-locking screws in other openings on plate. This can help further secure the bone plate to the bone fracture if needed. One advantage of opening 18 is that it is adapted to receive any one of the potential fasteners that may be used with plate 12.

In some instances, once all fasteners and/or screws are placed, the surgeon may place covers over the unused openings, particularly if there are any unused openings that cross the fracture in order to strengthen the plate 12. Additionally or alternatively, the surgeon may use bone graft material, bone cement, bone void filler, and any other material to help heal the bone.

Figure 16:
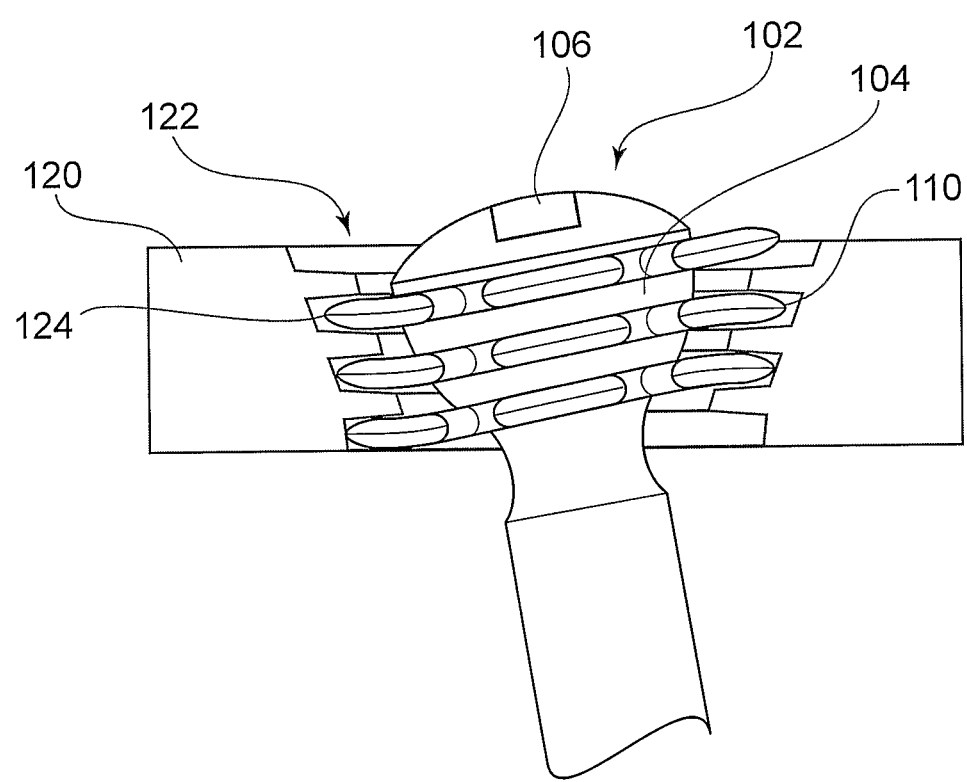
FIG. 16 shows a cross-section view of an alternate embodiment having a finned fastener in place in a bone plate.
Figure 17:
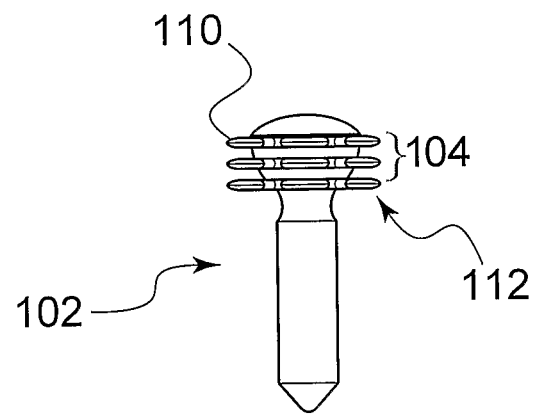
FIG. 17 shows a side perspective view of a fastener having a finned head according to one embodiment of the invention.
Figure 18:
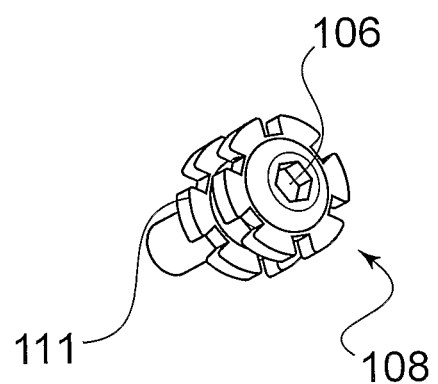
FIG. 18 shows a top perspective view of the fastener of FIG. 17.

An alternate embodiment of a fixation assembly is shown in FIGS. 16-18. These figures show a fastener 102 with a finned head 104. Specifically, the finned head 104 comprises a receiving bore 106 at its upper portion 108 and at least one set of extending fins 110 around the main portion 112 of the head 104. Fins 110 are shown as being square or trapezoidally-shaped with tapered edges, although they may be any other shape, such as rounded, oval, rectangular, curved, rhomboid, diamond-shaped, triangular or any other appropriate shape. The edges 111 of fins 110 may taper inwardly, outwardly, or be about parallel with one another. Fins 110 may be provided in a single row around head 104 or layered in multiple rows as shown. If layered in multiple rows, each individual fin 110 may be directly above another fin (so the top of the fastener 100 looks like that shown in FIG. 18). Alternatively, each individual fin 110 in a lower layer may be offset from a fin in a higher layer. The number of fins 24 in a set may also vary from about two or three up to any desired number that can fit on main portion 112 of head 104. As with the fins 24 of opening 18 described above, the fins 110 are preferably quite thin, the thickness varying depending upon the use of fastener and plate. For example, a larger fastener 102 for use with a larger plate (e.g., for use on a femur bone) will likely have larger and thicker fins 110 than a smaller fastener (e.g., for use on a smaller bone). In specific embodiments, the fins 110 are particularly thin so that they can be moved up or down or compressed upon pressure. A non-limiting exemplary range of thicknesses for fins may be from about 0.5 mm to about 5 mm, although larger and smaller sizes are possible. In theory, the fins 110 are intended to fit between the threadform of plate. Fastener may also have a shaft 114 that is threaded or unthreaded, as described above with respect to fastener 80.

Figure 19:
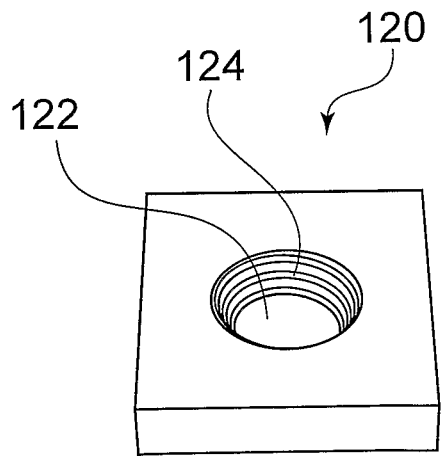
FIG. 19 shows a top perspective view of a bone plate that may be used to receive the fastener of FIGS. 17 and 18.
Figure 20:
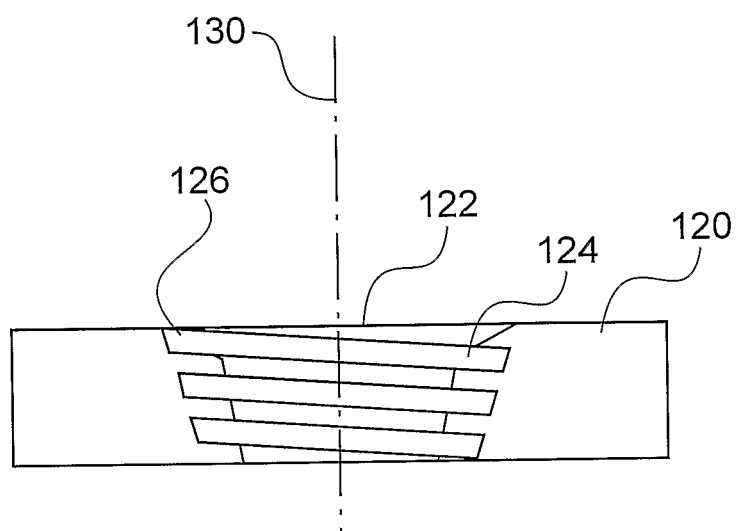
FIG. 20 shows a cross-section of the threads of the plate of FIG. 19.
Figure 21:
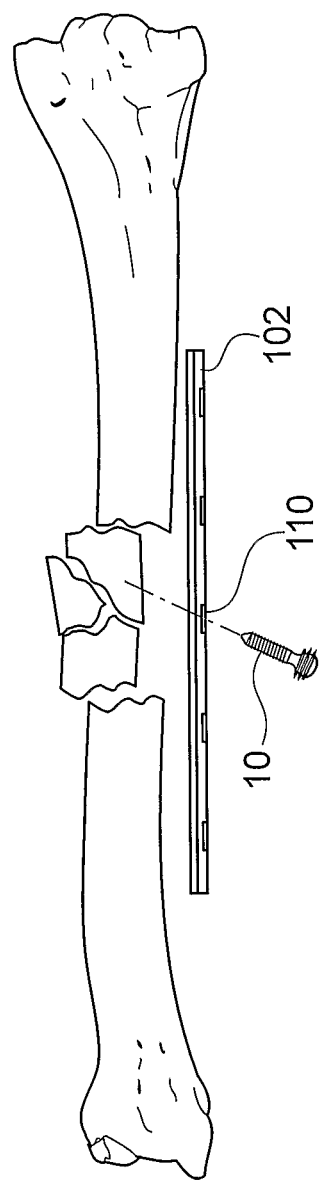
FIG. 21 shows an example of a fracture that may be treated with various embodiments of the invention.

Fastener 102 may be used with any bone plate that has a threaded opening. Any of the examples shown in the figures are described above may be used with fastener 102. One option of a specific bone plate that can be used with fastener 110 is shown in FIG. 19. This bone plate 120 has Acme threads 124 that have a more rectangular shape than the pointed, sharp threads that are typically used in bone plates. As shown in FIG. 20, opening 122 has threads 124 that end at their edges 126 in a rectangular shape. Providing a rectangular shape with a flatter edge 126 allows a larger channel for the fins 110 to engage. In an even more specific embodiment, the threads 124 may be angled at about 15-20° off of the central axis 130 of opening 122, and even more specifically, at about 18° off of the central axis 130.

An example of the method of use is similar to that describe above. As fastener 102 is being inserted into bone plate 120 (although it should be understood that any traditional bone plate may be used; Acme threads are not a requirement), the fins 110 are intended to engage threads of the plate and, much like the fins of the bone plate described above, fins 110 are very thin so that as the threads of plate start to grab the fins 110, the fins 110 may move up or down as appropriate to engage the threads of plate and secure the fastener 102 in place, as shown in FIG. 16. In most cases, this movement of fins 110 is a permanent deformation, so that the fins cannot flex back and allow the fastener to work its way out.

The foregoing description of exemplary embodiments of the invention has been presented only for the purposes of illustration and description and is not intended to be exhaustive or to limit the invention to the precise forms disclosed. Many modifications and variations to the structures and methods recited above and shown in the drawings are possible without departing from the scope or spirit of the above disclosure and the following claims. The embodiments were chosen and described in order to explain the principles of the invention and their practical application so as to enable others skilled in the art to make and utilize the invention and various embodiments and with various modifications as are suited to the particular use contemplated. Alternative embodiments will become apparent to those skilled in the art to which the present invention pertains without departing from its spirit and scope.

What is claimed is:

1. A polyaxial bone fixation system, the system comprising:
    (a) at least one fastener, the fastener being at least partially threaded and having a head portion and a shaft portion; and
    (b) a bone plate comprising a lower surface, an upper surface and at least one opening extending from the lower surface to the upper surface, wherein the opening is adapted to receive the fastener, the opening having an inner surface with a plurality of fins integrally connected to, and protruding from, the inner surface, the plurality of fins having bases that intersect the inner surface, the intersection between the bases and the inner surface defining a single plane, wherein upon insertion of the fastener into the opening, the plurality of fins can bend and engage within the threads to hold the fastener in place at a desired insertion angle such that the fastener may be inserted and retained at any one of a plurality of angles relative to the opening.

2. The polyaxial bone fixation system of claim 1, wherein the fins are provided as a series of concavely indented, inwardly protruding fins that are adapted to secure a threaded head of a fastener in place at varying angles.

3. The polyaxial bone fixation system of claim 1, wherein the opening is further defined by a round circumference at the upper surface and a jagged circumference formed by the protruding fins at the lower surface.

4. The polyaxial bone fixation system of claim 1, wherein the protruding fins form a concave portion of the inner surface.

5. The polyaxial bone fixation system of claim 1, wherein the fins have a tapered shape or a straight shape.

6. The polyaxial bone fixation system of claim 1, wherein the bone plate is adapted to contact a femur, a distal tibia, a proximal tibia, a proximal humerus, a distal humerus, a clavicle, a fibula, an ulna, a radius, bones of the foot, or bones of the hand.

7. The polyaxial bone fixation system of claim 1, wherein the bone plate has one or more of the following features:
    a bone plate that is contoured, straight or flat;
    a head portion that is contoured to match a particular bone surface;
    a head that flares out to form an L-shape, T-shape, or Y-shape; and any combination thereof.

8. The polyaxial bone fixation system of claim 1, wherein the bone plate has a head and the opening is located on the head.

9. The polyaxial bone fixation system of claim 1, wherein the bone plate further comprises one or more of the following openings:
    a threaded opening;
    a non-threaded opening;
    an opening adapted to receive locking or non-locking fasteners;
    an opening with fins;
    a provisional fixation opening;
    a combination slot; or
    any combination thereof.

10. The polyaxial bone fixation system of claim 1, wherein the fins are trapezoidally-shaped, rounded, oval, rectangular, curved, rhomboid, diamond-shaped, or triangular.

11. The polyaxial bone fixation system of claim 1, wherein the edges of fins taper inwardly, outwardly, or are about parallel with one another.

12. The polyaxial bone fixation system of claim 1, wherein the fins are bending so that the fins are interposed between the threads of the fastener.

13. The polyaxial bone fixation system of claim 1, wherein the single plane defined by the intersection between the bases and the inner surface is curved to correspond to the contour of the bone plate.

14. The polyaxial bone fixation system of claim 1, wherein the single plane is defined by the intersection between the bases of three or more fins and the inner surface.

15. The polyaxial bone fixation system of claim 1, wherein the single plane is defined by the intersection between the bases of at least five and no more than eight fins and the inner surface.

16. The polyaxial bone fixation system of claim 1, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

17. A polyaxial bone fixation system, the system comprising:
    (a) at least one fastener, the fastener being at least partially threaded and having a head portion and a shaft portion; and
    (b) a bone plate comprising a lower surface, an upper surface and at least one opening extending from the lower surface to the upper surface, wherein the opening is adapted to receive the fastener, the opening having an inner surface with a plurality of fins integrally connected to, and protruding from, the inner surface, the plurality of fins having bases that intersect the inner surface, the intersection between the bases and the inner surface defining a single plane, wherein upon insertion of the fastener into the opening, the plurality of fins can bend and engage within the threads to hold the fastener in place at a desired insertion angle such that the fastener may be inserted and retained at any one of a plurality of angles relative to the opening, the fins bending so that the fins are interposed between the threads of the fastener.

18. The polyaxial bone fixation system of claim 17, wherein the single plane defined by the intersection between the bases and the inner surface is curved to correspond to the contour of the bone plate.

19. The polyaxial bone fixation system of claim 17, wherein the single plane is defined by the intersection between the bases of three or more fins and the inner surface.

20. The polyaxial bone fixation system of claim 17, wherein the single plane is defined by the intersection between the bases of at least five and no more than eight fins and the inner surface.

21. The polyaxial bone fixation system of claim 17, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

22. A polyaxial bone fixation system, the system comprising:
   (a) at least one fastener, the fastener being at least partially threaded and having a head portion and a shaft portion; and
   (b) a bone plate comprising a lower surface, an upper surface and at least one opening extending from the lower surface to the upper surface, wherein the opening is adapted to receive the fastener, the opening having an inner surface with a plurality of fins integrally connected to, and protruding from, the inner surface and generally conforming to the lower surface, the plurality of fins having bases that intersect the inner surface, the intersection between the bases and the inner surface defining a single plane, wherein upon insertion of the fastener into the opening, the plurality of fins can bend and engage within the threads to hold the fastener in place at a desired insertion angle such that the fastener may be inserted and retained at any one of a plurality of angles relative to the opening.

23. The polyaxial bone fixation system of claim 22, wherein the single plane defined by the intersection between the bases and the inner surface is curved to correspond to the contour of the bone plate.

24. The polyaxial bone fixation system of claim 22, wherein the single plane is defined by the intersection between the bases of three or more fins and the inner surface.

25. The polyaxial bone fixation system of claim 22, wherein the single plane is defined by the intersection between the bases of at least five and no more than eight fins and the inner surface.

26. The polyaxial bone fixation system of claim 22, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

27. A polyaxial bone fixation system, the system comprising:
   (a) at least one fastener, the fastener being at least partially threaded and having a head portion and a shaft portion; and
   (b) a bone plate comprising a lower surface, an upper surface and at least one opening extending from the lower surface to the upper surface, the opening having an inner surface with a plurality of at least 3, but no more than 10, fins integrally connected to, and protruding from, the inner surface, the plurality of fins having bases that intersect the inner surface, the intersection between the bases and the inner surface defining a single plane, wherein upon insertion of the fastener into the opening, the plurality of fins can bend and engage within the threads to hold the fastener in place such that the fastener may be inserted and retained at any one of a plurality of angles relative to the opening.

28. The polyaxial bone fixation system of claim 27, wherein the single plane defined by the intersection between the bases and the inner surface is curved to correspond to the contour of the bone plate.

29. The polyaxial bone fixation system of claim 27, wherein the single plane is defined by the intersection between the bases of three or more fins and the inner surface.

30. The polyaxial bone fixation system of claim 27, wherein the single plane is defined by the intersection between the bases of at least five and no more than eight fins and the inner surface.

31. The polyaxial bone fixation system of claim 27, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

32. A polyaxial bone fixation system, the system comprising:
   (a) at least one fastener, the fastener being at least partially threaded and having a head portion and a shaft portion; and
   (b) a bone plate comprising a lower surface, an upper surface and at least one opening extending from the lower surface to the upper surface, wherein the opening is adapted to receive the fastener, the opening having an inner surface with a plurality of fins integrally connected to, and protruding from, the inner surface, and the fins having a concave upper surface portion at or near the inner surface, the plurality of fins having bases that intersect the inner surface, the intersection between the bases and the inner surface defining a single plane, wherein upon insertion of the fastener into the opening, the plurality of fins can bend and engage within the threads to hold the fastener in place at a desired insertion angle such that the fastener may be inserted and retained at any one of a plurality of angles relative to the opening.

33. The polyaxial bone fixation system of claim 32, wherein the single plane defined by the intersection between the bases and the inner surface is curved to correspond to the contour of the bone plate.

34. The polyaxial bone fixation system of claim 32, wherein the single plane is defined by the intersection between the bases of three or more fins and the inner surface.

35. The polyaxial bone fixation system of claim 32, wherein the single plane is defined by the intersection between the bases of at least five and no more than eight fins and the inner surface.

36. The polyaxial bone fixation system of claim 32, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

37. A polyaxial bone fixation system, the system comprising:
   (a) at least one fastener, the fastener being at least partially threaded and having a head portion and a shaft portion; and
   (b) a bone plate comprising a lower surface, an upper surface and at least one opening extending from the bone conforming arcuate lower surface to the upper surface, wherein the opening is adapted to receive the fastener, the opening having an inner surface with a plurality of fins, the fins generally conforming to the shape of the lower surface, and having a concave upper surface portion at or near the inner surface, the plurality of fins having bases that intersect the inner surface, the intersection between the bases and the inner surface defining a single plane, wherein upon insertion of the fastener into the opening, the plurality of fins can bend and engage within the threads to hold the fastener in place at a desired insertion angle such that the fastener may be inserted and retained at any one of a plurality of angles relative to the opening.

38. The polyaxial bone fixation system of claim 37, wherein the single plane defined by the intersection between the bases and the inner surface is curved to correspond to the contour of the bone plate.

39. The polyaxial bone fixation system of claim 37, wherein the single plane is defined by the intersection between the bases of three or more fins and the inner surface.

40. The polyaxial bone fixation system of claim 37, wherein the single plane is defined by the intersection between the bases of at least five and no more than eight fins and the inner surface.

41. The polyaxial bone fixation system of claim 37, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

42. A polyaxial bone fixation system, the system comprising:
   (a) at least one fastener, the fastener being at least partially threaded and having a head portion and a shaft portion; and
   (b) a bone plate comprising a lower surface, an upper surface and at least one opening extending from the lower surface to the upper surface, wherein the opening is adapted to receive the fastener, the opening having an inner surface with a plurality of fins integrally connected to, and protruding from, the inner surface, the fins generally conforming to the shape of the lower surface, and having a concave upper surface portion at or near the inner surface, the plurality of fins having bases that intersect the inner surface, the intersection between the bases and the inner surface defining a single plane, wherein upon insertion of the fastener into the opening, the plurality of fins can bend and engage within the threads to hold the fastener in place at a desired insertion angle such that the fastener may be inserted and retained at any one of a plurality of angles relative to the opening, the fins bending so that the fins are interposed between the threads of the fastener.

43. The polyaxial bone fixation system of claim 42, wherein the single plane defined by the intersection between the bases and the inner surface is curved to correspond to the contour of the bone plate.

44. The polyaxial bone fixation system of claim 42, wherein the single plane is defined by the intersection between the bases of three or more fins and the inner surface.

45. The polyaxial bone fixation system of claim 42, wherein the single plane is defined by the intersection between the bases of at least five and no more than eight fins and the inner surface.

46. The polyaxial bone fixation system of claim 42, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

47. A polyaxial bone fixation system, the system comprising:
   a bone plate comprising a lower surface, an upper surface, and at least one opening extending from the lower surface to the upper surface, wherein the opening is configured to receive a fastener, the opening having an inner surface with a plurality of fins protruding from the inner surface, the plurality of fins having bases that intersect the inner surface, the intersection between the bases and the inner surface defining a single plane, wherein the plurality of fins can bend relative to a head portion of the fastener when the fastener is inserted into the opening such that the fastener may be inserted and retained at any one of a plurality of angles relative to the opening.

48. The polyaxial bone fixation system of claim 47, further comprising at least one fastener, the fastener being at least partially threaded and having a head portion and a shaft portion.

49. The polyaxial bone fixation system of claim 47, wherein the single plane defined by the intersection between the bases and the inner surface is curved to correspond to the contour of the bone plate.

50. The polyaxial bone fixation system of claim 47, wherein the single plane is defined by the intersection between the bases of three or more fins and the inner surface.

51. The polyaxial bone fixation system of claim 47, wherein the single plane is defined by the intersection between the bases of at least five and no more than eight fins and the inner surface.

52. The polyaxial bone fixation system of claim 47, wherein the at least one opening of the bone plate defines a central axis, and wherein the single plane defined by the intersection between the bases and the inner surface is orthogonal to the central axis such that, upon insertion of the fastener into the opening, the fastener may be retained at any one of a plurality of angles relative to the central axis.

* * * * *